(12) United States Patent
Jarvis

(10) Patent No.: US 9,045,778 B2
(45) Date of Patent: Jun. 2, 2015

(54) INSECT CELL LINE FOR PRODUCTION OF RECOMBINANT GLYCOPROTEINS WITH SULFATED COMPLEX N-GLYCANS

(75) Inventor: Donald L. Jarvis, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 859 days.

(21) Appl. No.: 12/421,977

(22) Filed: Apr. 10, 2009

(65) Prior Publication Data

US 2009/0288178 A1     Nov. 19, 2009

Related U.S. Application Data

(63) Continuation-in-part of application No. PCT/US2007/080997, filed on Oct. 10, 2007.

(60) Provisional application No. 60/850,573, filed on Oct. 10, 2006.

(51) Int. Cl.
*A01N 63/00* (2006.01)
*C12N 15/85* (2006.01)

(52) U.S. Cl.
CPC ......... *C12N 15/8509* (2013.01); *A01K 2217/05* (2013.01); *A01K 2227/706* (2013.01); *A01K 2267/01* (2013.01); *C12N 2799/026* (2013.01)

(58) Field of Classification Search
None
See application file for complete search history.

(56) References Cited

U.S. PATENT DOCUMENTS

| | | | | |
|---|---|---|---|---|
| 6,461,863 | B1 * | 10/2002 | Jarvis | 435/320.1 |
| 6,518,064 | B1 | 2/2003 | Miller et al. | |
| 2005/0181359 | A1 | 8/2005 | Optelten et al. | |
| 2005/0287637 | A1 | 12/2005 | Betenbaugh et al. | |

OTHER PUBLICATIONS

Betenbaugh et al. Curr Opin Structural Biol 2004;14:601-6.*
El-Fasakhany et al. J Biochem 2003;133:287-93.*
Suzuki et al. J Biol Chem 2001;276:24388-395.*
Marth et al. Chaper 7 in Essentials of Glycobiology Ed. Varki et al. Cold Spring Harbor Laboratory Press 1999.*
Wagner et al. J Virol 1996;70:4103-9.*
Togame et al. Analyt Biochem 2003;315:67-76.*
Kamiyama et al. J Bio Chem 2003;278:25958-63.*
Aumiller, J. J., et al. "A transgenic insect cell lune engineered to produce CMP-sialic acid and sialylated glycoproteins." Glycobiology, 13(6): 497-507 (2003).
Hollister, J., et al. "Engineering the Protein Glycosylation Pathway in Insect Cells for Production of Biantennary, Complex N-Glycans," Biochemistry, 41: 15093-15104 (2002).
Harrison, R. L., et al. "Protein N-glycosylation in the baculovirus-insect cell expression system and engineering of insect cells to produce 'mammalianized' recombinant glycoproteins." Advances in Virus Research, 68: 159-191 (Sep. 22, 2006).
Hollister, J. R., et al. "Engineering lepidopteran insect cells for sialoglycoprotein production by genetic transformation with mammalian β1,4-galactosyltransferase and α2,6-sialyltransferase genes." Glycobiology, 11(1): 1-9 (2001).
Shi, X., et al. "Protein N-Glycosylation in the Baculovirus-Insect Cell System." Current Drug Targets, 8: 116-1125 (2007).
Karaivanova, V. K, et al. "Sulphation of N-linked oligosaccharides of *Vesicular stomatitis* stomatitis and influenza virus envelope glycoproteins: host cell specificity, subcellular localization and indentification of substituted saccharides." Biochemical Journal, 329: 511-518 (1998).
Chandrasekaran, E. V., et al. "Identification of Physiologically Relevant Substrates for Cloned Gal: 2-O-Sulfotransferases (Gal3STs)." Journal of Biological Chemistry, 279(11): 10032-10041 (2004).
El-Fasakhany, F. M., et al. "N-acetylglucosamine-6-O-sulfotransferase-1: production in the baculovirus system and its application to the synthesis of a sulfated oligosaccharide and to the modification of oligosaccharides in fibrinogen." Journal of Biochemistry, 133(3): 287-293 (Mar. 2003) (Abstract).

* cited by examiner

*Primary Examiner* — Janice Li
(74) *Attorney, Agent, or Firm* — Kathleen D. Rigaut; Robert C. Netter; Dann, Dorfman, Herrell & Skillman

(57) ABSTRACT

A transgenic insect cell line for production of recombinant glycoproteins possessing sulfated, complex N-glycans is provided.

32 Claims, 14 Drawing Sheets

GnTII and GalT Activities Induced by GnTII/GalT Vector

Transgene Expression (Gal T Activity)

Sulfo-T Activity Assays

A

B

Recombinant gP Production Levels rHA Product Analysis

```
                              SEQUENCE LISTING

<160> NUMBER OF SEQ ID NOS: 14

<210> SEQ ID NO 1
<211> LENGTH: 52
<212> TYPE: DNA
<213> ORGANISM: Artificial Sequence
<220> FEATURE:
<223> OTHER INFORMATION: primer

<400> SEQUENCE: 1
ggtaccgttt aaacggatcc actagtgggc ccgcctcgac tgtgccttct ag          52

<210> SEQ ID NO 2
<211> LENGTH: 51
<212> TYPE: DNA
<213> ORGANISM: Artificial Sequence
<220> FEATURE:
<223> OTHER INFORMATION: primer

<400> SEQUENCE: 2
aagcttataa cgtctagagt taacgtcgac tccccagcat gcctgctatt g           51

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tcgcgaatga aggtgttccg t                                            21

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gcggccgctt agagacgggg ctt                                          23

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
```
ggtaccatga tgtccttgct g                                              21

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gtttaaacct acgcccccag gaac                                           24

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gtcgacatgc gtaaaattga c                                              21

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
gttaacattc gataaaagtt ttgttac                                        27

<210> SEQ ID NO 9
<211> LENGTH: 51
<212> TYPE: DNA
<213> ORGANISM: Artificial Sequence
<220> FEATURE:
<223> OTHER INFORMATION: primer

<400> SEQUENCE: 9
aagcttataa cgtctagaag gcctgtcgac tccccagcat gcctgctatt g             51

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gtttaaacat gaggctccgc aatg                                           24

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
actagttcag ttggtggctt t                                              21

<210> SEQ ID NO 12
<211> LENGTH: 21
<212> TYPE: DNA
<213> ORGANISM: Artificial Sequence -continued

```
<220> FEATURE:
<223> OTHER INFORMATION: primer

<400> SEQUENCE: 12
tcgcgaatga gacgctacaa g                                           21

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ctcgagctag acttccgcct cg                                          22

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
aggcctattc gataaaagtt ttgttac                                     27
```

INSECT CELL LINE FOR PRODUCTION OF RECOMBINANT GLYCOPROTEINS WITH SULFATED COMPLEX N-GLYCANS

This application is a 35 U.S.C. §365(c) continuation-in-part application of PCT/US07/80997, filed on Oct. 10, 2007, which claims priority under 35 U.S.C. §119(e) to U.S. Provisional Application, 60/850,573, filed Oct. 10, 2006. The foregoing applications are incorporated by reference herein.

FIELD OF THE INVENTION

This invention relates to the fields of molecular biology and the production of therapeutically important glycoproteins in insect cell lines.

BACKGROUND OF THE INVENTION

Several publications and patent documents are cited throughout the specification in order to describe the state of the art to which this invention pertains. Each of these citations is incorporated herein by reference as though set forth in full.

Many biomedically significant proteins, including antibodies, cytokines, anticoagulants, blood clotting factors, and others are glycoproteins. Thus, there is a high demand for systems that can be used to produce recombinant glycoproteins for basic biomedical research and direct clinical applications. Unfortunately, few currently available recombinant protein production systems can produce higher eukaryotic glycoproteins with authentic carbohydrate side chains. Furthermore, no currently available system can produce large amounts of recombinant glycoproteins in properly glycosylated form at relatively low cost.

The glycoproteins are a major subclass of proteins distinguished by the presence of oligosaccharide side chains, or glycans, covalently linked to the polypeptide backbone. It has been estimated that over half of the proteins encoded by the human genome are modified by glycosylation and this subclass includes many different types of biomedically significant proteins, as noted above. Furthermore, glycoprotein glycans are much more than mere chemical decorations of the polypeptide backbone. In fact, glycoprotein glycans have been implicated in a wide variety of important biochemical and biological functions, including protein stability, trafficking, serum half-life, immune function, enzymatic function, cellular adhesion, and others.

Influenza viruses are enveloped, single stranded RNA viruses with two type I membrane glycoproteins, hemagglutinin (HA) and neuraminidase (NA), projecting from the virion surface. Each year, seasonal influenza affects 3-5 million people worldwide and causes 300,000-500,000 fatalities. A pandemic outbreak of a new influenza virus strain, like the one that occurred in 1918, could kill tens of millions of people worldwide. Vaccination is the most effective means of preventing influenza infections. Antibodies induced against HA's are protective; thus, HA content is used to standardize influenza vaccines. Seasonal influenza vaccines consist of three strains of influenza, including two strains of influenza A and one of influenza B. New strains of influenza viruses can appear relatively frequently. Thus, the WHO and CDC recommends which strains to include in influenza vaccines and this can change each year. Currently, most approved influenza vaccines are produced in embryonated chicken eggs. These vaccines consist of inactivated whole or split subunit preparations. Production of these vaccines involves the adaptation of selected viral strains for high yield in eggs by either serial passage or reassortment with other high-yield strains. The selected influenza viruses are then mass-produced in chicken eggs, the progeny are purified from allantoic fluid and whole or split virus preparations are inactivated with a chemical agent such as formaldehyde. Egg-based vaccine production is time consuming, requires large biocontainment facilities, and relies upon the availability of millions of eggs. In the event of a pandemic outbreak, especially one involving a highly pathogenic avian influenza virus such as H5N1, these would be deadly limitations. Cell culture-based vaccine production using recombinant DNA technology, rather than live influenza virus, can overcome all of these limitations.

As mentioned above, the native HA molecule has covalently linked oligosaccharide side chains. Influenza HA's are classified as N-glycoproteins because their glycans are linked via amide (N), rather than glycosidic (O) bonds to the polypeptide chain. Different strains of influenza viruses can have variable numbers and types of N-glycans. The N-glycans at some sites on the HA polypeptide have high mannose structures, while those at others have a variety of more highly processed, complex structures (3, 7, 25, 27, 35, 37, 50). In fact, in a population of HA molecules, the same glycosylation site is typically occupied by a variety of different N-glycan species. One major type of complex N-glycan found on influenza HA's is a terminally galactosylated, biantennary structure with or without a bisecting N-acetylglucosamine residue, which also can have sulfated N-acetylglucosamine and galactose residues. Other types of complex N-glycans found on HA's are terminally galactosylated, tri- and tetraantennary structures.

In summary, existing vaccines are produced in eggs, which is a slow, unreliable, and potentially dangerous process. Clearly, alternative systems for influenza virus vaccine production are badly needed.

SUMMARY OF THE INVENTION

In accordance with the present invention, a transgenic insect cell, for example, a cell line, for the production of at least one protein of interest comprising sulfated complex N-glycans is provided. An exemplary cell comprises at least two of the following modifying enzymes, particularly at least two of the modifying enzymes encoded by nucleic acids: i) —N-acetylglucosaminyltransferase II; ii) —N-acetylglucosaminyltransferase III; iii) —N-acetylglucosaminyltransferase IV; iv) -Beta 1,4-Galactosyltransferase; v) —N-acetylglucosamine-6-O-sulfotransferase; vi) -Galactose-3-O-sulfotransferase; vii) —N-acetylglucosaminyltransferase V, and, optionally, at least one nucleic acid encoding at least one protein of interest, wherein said modifying enzymes catalyze the formation of sulfated complex N-glycans on the protein(s) of interest.

In one embodiment of the invention, the cell line contains both at least one of the recombinant nucleic acids encoding the modifying enzymes described above as well as one or more nucleic acids encoding the protein(s) of interest. Alternatively, the cell line comprises at least one of the recombinant nucleic acids encoding the modifying enzymes only, and the nucleic acid(s) encoding the protein(s) of interest is introduced in a separate expression vector. Exemplary proteins of interest can include, without limitation, a subunit vaccine, antibody, cytokine, blood clotting factor, anticoagulant, viral antigen, enzyme, receptor, vaccine, and hormone.

Preferred cells for use in the invention include those isolated from lepidopteran, coleopteran, hymenopteran, or dipteran insects. Most preferably, the cells are obtained from Lepidoptera.

In yet another aspect of the invention, a method for producing at least one protein of interest comprising sulfated complex N-glycans is provided. An exemplary method entails providing a cell as described above, introducing a nucleic acid encoding at least one protein of interest into the cell comprising the modifying enzymes, and incubating the cell under conditions which result in production of said enzymes and said protein of interest, the protein of interest so produced comprising sulfated complex N-glycans. The method optionally entails isolation of the at least one protein of interest.

In another embodiment of the invention, a transgenic insect, or progeny thereof, for the production of at least one protein of interest comprising sulfated complex N-glycans is disclosed. An exemplary insect comprises at least one nucleic acid encoding at least two of the following modifying enzymes: 1) —N-acetylglucosaminyltransferase II; ii) —N-acetylglucosaminyltransferase III; iii) —N-acetylglucosaminyltransferase IV; iv) -Beta 1,4-Galactosyltransferase; v) —N-acetylglucosamine-6-O-sulfotransferase; vi) -Galactose-3-O-sulfotransferase; vii) —N-acetylglucosaminyltransferase V, and, optionally, nucleic acids encoding at least one said protein(s) of interest, wherein said modifying enzymes encoded thereby are effective to catalyze the formation of sulfated complex N-glycans on said protein(s) of interest. As above, the insect may comprise at least one of the nucleic acid encoding the modifying enzymes discussed above as well as the nucleic acid encoding the protein(s) of interest. Alternatively, the insect cells may comprise at least one of the nucleic acids encoding the modifying enzymes only while the nucleic acid encoding the protein(s) of interest is introduced into the insect on a separate expression vector. The invention also entails a method for producing a protein of interest comprising sulfated complex N-glycans in the insects described above.

Finally, another aspect of the invention encompasses a kit for the production of at least one protein of interest comprising sulfated complex N-glycans is provided. In this aspect of the invention, at least two of the nucleic acids encoding the modifying enzymes described above are introduced into an insect cell under conditions suitable for the enzymes to catalyze formation of sulfated complex N-glycans on said protein(s) of interest. The kit further comprises insect cells. In another aspect, the kit comprises at least one nucleic acid encoding at least one protein of interest. The kit optionally comprises methods for the isolation of the protein(s) of interest from the cell.

DETAILED DESCRIPTION OF THE INVENTION

Figure 1A:
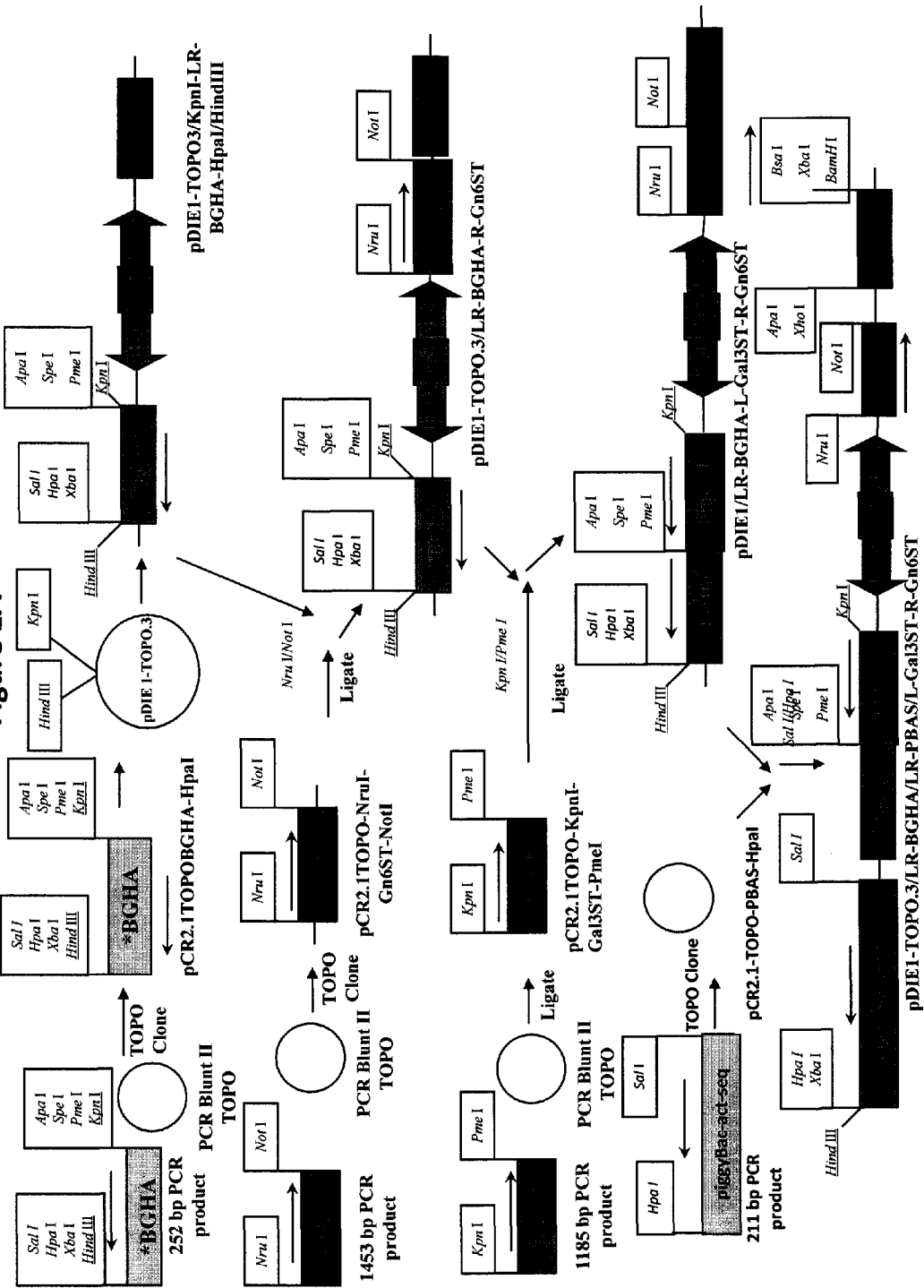
FIG. 1A is a schematic diagram depicting the construction of a dual piggyBac vector encoding the Gal3ST and Gn6ST genes.

In accordance with the present invention, new, transgenic insect cell lines which produce recombinant glycoproteins with sulfated, complex type oligosaccharide side chains, or N-glycans are provided. Insect cells are widely used alone or as hosts for baculovirus expression vectors to produce recombinant glycoproteins [1]. However, insect cell protein N-glycosylation pathways are more primitive than those of higher eukaryotes. Thus, recombinant glycoproteins produced using insect cell systems typically have relatively simple "paucimannosidic" type N-glycans in place of the "complex" type structures found on native higher eukaryotic glycoproteins [2]. The complex type structures on the native products can be functionally significant in a wide variety of ways. Thus, the relatively limited N-glycan processing capabilities of insect cells limit their practical applications for recombinant glycoprotein production. This problem can be addressed by using genetic engineering to permanently introduce mammalian genes encoding N-glycan processing functions into insect cell genomes. This general approach can be used to create transgenic insect cell lines or insects encoding more extensive, relatively "humanized" N-glycosylation pathways. While 1) mammalian glycosyltransferase genes have been successfully introduced into insect cells, 2) transgenic subclones that encode and express the functions encoded by these genes have been isolated, and 3) these subclones can produce more authentic recombinant glycoproteins [3], genetically engineered insect cells which produce sulfated, complex type N-glycans have not yet been developed.

While production of a commercial subunit vaccine directed against influenza viruses, including potentially pandemic influenza viruses is described herein, the present compositions and methods can be utilized to produce any medically beneficial glycoprotein (including vaccines, therapeutics, and diagnostics) which requires sulfated complex N-glycans. A small selection of additional examples of glycoproteins with this type of N-glycans include the vesicular stomatitis virus G glycoprotein (Karaivanova, V. K. and Spiro, R. G., (1998) Sulphation of N-linked oligosaccharides of vesicular stomatitis and influenza envelope glycoproteins: host cell specificity, subcellular localization and identification of substituted saccharides. Biochem. J. 329:511-518), the human immunodeficiency virus gp120 protein (A Shilatifard, R K Merkle, D E Helland, J L Welles, W A Haseltine, and R D Cummings, (1993) Complex-type N-linked oligosaccharides of gp120 from human immunodeficiency virus type 1 contain sulfated N-acetylglucosamine. J. Virol. 67:943-952), and the human plasma alpha 1 acid glycoprotein (Hermentin P, Witzel R, Doenges R, Bauer R, Haupt H, Patel T, Parekh R B, and Brazel D., (1992) The mapping by high-pH anion-exchange chromatography with pulsed amperometric detection and capillary electrophoresis of the carbohydrate moieties of human plasma alpha 1-acid glycoprotein. Anal Biochem. 206:419-429), among many others (see Roux, L., Holojda, S., Sundblad, G., Freeze, H., and Varki, A., (1988) Sulfated N-linked oligosaccharides in mammalian cells I. Complex-type chains with sialic acids and O-sulfated esters. J. Biol. Chem. 263:8879-8889 and references therein).

A baculovirus-insect cell expression system for scaled up production of this flu vaccine has been developed and the vaccine can be used to safely induce a protective immune response in human subjects in a variety of clinical trials [4]. However, given that insect cells lack several of the enzymes required to produce sulfated complex N-glycans, it was hypothesized that subunit vaccines possessing authentic mammalized glycosylation patterns may exhibit increased efficacy. Accordingly, one would expect that the presence of these N-glycans will alter the immune response to such molecules and thus it was proposed to investigate the influence of the insect cell-derived N-glycans on the immune response to the nascent subunit vaccine (FluBlØk®).

The BEVS.

The baculovirus expression vector system (BEVS) is the best-known insect system for recombinant protein production. The BEVS is a eukaryotic system that has been widely used for recombinant glycoprotein production, despite its limited N-glycan processing capabilities. In fact, the product expressed in the first report of the BEVS system was a human glycoprotein, β-interferon. Since then, the BEVS has been used to produce many different recombinant glycoproteins, facilitating biomedical research on their structure, function, and roles in human diseases. In addition to its utility for basic research, the BEVS also has been widely used in the biotechnology industry to produce recombinant glycoproteins intended for direct clinical use as vaccines, therapeutics, or diagnostic reagents. Protein Sciences: (proteinsciences.com) exclusively uses the BEVS to produce subunit vaccine candidates against the influenza and SARS viruses. Human clinical trials have shown that one of their influenza vaccine candidates, FluBlok®, is safe and efficacious and the FDA has given this product "fast-track" status. Dendreon: (dendreon.com) has used the BEVS to produce a therapeutic vaccine against prostate cancer (Provenge®). Successful human clinical trials led to fast-track status for this product, as well, and this led some to predict that Provenge® will be the first therapeutic cancer vaccine to reach the market. These examples highlight ways in which BEVS technology has facilitated basic and applied biomedical research. The salient point is that development of this insect-based system for recombinant glycoprotein production was a broadly significant accomplishment that is highly likely to have a huge impact on human health.

Herein, a transgenic insect cell line with the ability to support baculovirus-mediated production of a new form of (FluBlØk®), which possesses authentic N-glycans is provided. HA, as well as the envelope glycoproteins of some other important viruses, such as vesicular stomatitis virus and human immunodeficiency virus, have quite unusual complex N-glycan structures in which the core and/or peripheral N-acetylglucosamine and the peripheral galactose residues are sulfated [5-11]. Reactions leading to sulfation of these residues in higher eukaryotes are catalyzed by a family of enzymes known as the sulfotransferases [12-15]. Importantly, the presence of sulfate residues on HA are highly likely to be functionally significant because they contribute negative charges, which are known to be important for glycoprotein properties and functions, such as serum half lives, in mammalian systems. This is particularly important for HA because negative charges on glycoprotein glycans are usually contributed by terminal sialic acid residues, but these negative charges are lost when HA is desialylated by the influenza virus neuraminidase (NA) during the normal process of influenza virus maturation. Thus, it is clear that engineering an insect cell line such that it is capable of producing recombinant influenza HA with humanized N-glycans represents a significant advance in the art.

DEFINITIONS

The phrase "modifying enzymes" refers to the enzymes required to produce sulfated complex N-glycan in cells that do not produce such enzymes endogenously. Such enzymes can be expressed in cells via introduction of nucleic acids encoding the same, particularly in one or more expression vectors.

The phrase "complex N-glycan" refers to complex oligosaccharides with two or more branches, each containing at least one N-acetylglucosamine, galactose, and sialic acid residue.

A "cell" or "cell line" refers to protein N-linked oligosaccharides in which both of the core mannose residues are substituted with monosaccharides other than mannose.

As used herein, the term "insect" includes any stage of development of an insect, including a one-celled germ line cell, a fertilized egg, an early embryo, a larva, including any of a first through a fifth instar larva, a pupa, or an adult insect. For the production of mammalianized polypeptides of interest, a large larva, such as a fourth or fifth instar larva is preferred. It will be evident to a skilled worker which insect stage is suitable for a particular purpose, such as for direct production of a glycosylated polypeptide of interest, for storage or transport of an insect to a different location, for generation of progeny, for further genetic crosses, or the like. Exemplary insects include without limitation, lepidopteran insects such as, *Spodoptera frugiperda, Trichoplusia ni, Bombyx mori*, and *Drosophila melanogaster*.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (on the World Wide Web at: (ncbi.nlm.nih.gov/blast/); Altschul et al., 1990, J Mol Biol 215:403-410) using a gapped alignment with default parameters, may be used to determine the level of identity and similarity between nucleic acid sequences and amino acid sequences.

The term "expression control sequence", as used herein, refers to a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc.

Suitable expression control sequences that can function in insect cells will be evident to the skilled worker. In some embodiments, it is desirable that the expression control sequence comprises a constitutive promoter. Among the many suitable "strong" promoters which can be used are the baculovirus promoters for the p10, polyhedrin (polh), p6.9, capsid, and cathepsin-like genes. Among the many "weak" promoters which are suitable are the baculovirus promoters for the ie1, ie2, ie0, et1, 39K (aka pp31), PE-38, and gp64 genes. Other suitable strong constitutive promoters include the *B. mori* actin gene promoter; *Drosophila melanogaster* hsp70, actin, α-1-tubulin or ubiquitin gene promoters; RSV or MMTV promoters; copia promoter; gypsy promoter; and the cytomegalovirus IE gene promoter. If it is desired to increase the amount of gene expression from a weak promoter, enhancer elements, such as the baculovirus enhancer element, hr5, may be used in conjunction with the promoter.

In some embodiments, the expression control sequence comprises a tissue—or organ—specific promoter. Many such expression control sequences will be evident to the skilled worker.

In general, the glycosylating enzymes of the invention are required in catalytic amounts. Therefore, in one embodiment of the invention, much lower amounts of these enzymes are present than of the heterologous polypeptides of interest, which are generated in massive, large amounts, glycosylated, and harvested for further use. For example, a suitable molar ratio of heterologous protein produced to a glycosylating enzyme may be greater than about 100:1.

Alternatively, the glycosylating enzymes may be in comparable (e.g., approximately stoichiometric) amounts to the heterologous protein(s) to be glycosylated. A skilled worker can readily select suitable promoters and/or conditions to express suitable amounts of the glycosylating enzymes (e.g., amounts which are sufficient to (effective to) glycosylate relatively high amounts of a protein of interest). Furthermore, a skilled worker can readily ensure that the glycosylation enzymes are present in sufficient local concentrations, and at an optimal time during insect propagation.

In some embodiments of the invention, as is discussed in more detail elsewhere herein, it is desirable that an expression control sequence is regulatable (e.g., comprises an inducible promoter and/or enhancer element). Suitable regulatable promoters include, e.g., *Drosophila* or other hsp70 promoters, the *Drosophila* metallothionein promoter, an ecdysone-regulated promoter, the *Saccharomyces cerevisiae* Gal4/UAS system, and other well-known inducible systems. A Tet-regulatable molecular switch may be used in conjunction with any constitutive promoter, such as those described elsewhere herein (e.g., in conjunction with the CMV-IE promoter, or baculovirus promoters). Another type of inducible promoter is a baculovirus late or very late promoter that is only activated following infection by a baculovirus.

Methods for designing and preparing constructs suitable for generating transgenic insect cell lines or insects (or vectors for infection of an insect) are conventional. For these methods, as well as other molecular biology procedures related to the invention, see, e.g., Sambrook et al., Molecular Cloning: A Laboratory Manual, Second Edition, Cold Spring Harbor, N.Y., (1989); Wu et al, Methods in Gene Biotechnology (CRC Press, New York, N.Y., 1997), Recombinant Gene Expression Protocols, in Methods in Molecular Biology, Vol. 62, (Tuan, ed., Humana Press, Totowa, N.J., 1997); and Current Protocols in Molecular Biology, (Ausabel et al, Eds.), John Wiley & Sons, NY (1994-1999). Some suitable methods are described elsewhere herein.

A variety of immortalized lepidopteran insect cell lines are suitable for transformation by the vectors/constructs of the invention. Among these are Sf21 (Vaughn et al. (1977) In Vitro 13, 213-217), Sf9, Tn 5B1-4 (High Five®; Wickham et al. (1992) Biotech. Progr. 8, 391-6), ExpresSf+® (Protein Sciences Corporation), and BmN cells.

Methods for generating transgenic insect cell lines are conventional. For example, in one embodiment, one or more genes to be introduced are placed under the control of a suitable expression control sequence and are cloned into one or more plasmid vectors. These vectors are then mixed with a vector encoding a selectable marker under the control of a suitably expression control sequence. The DNA mixture is then introduced into the parental insect cell line (e.g., by calcium phosphate-mediated transfection), and the transgene(s) will integrate by non-homologous recombination into in the insect cell genome. Transformed cells are selected using an appropriate antibiotic (e.g. neomycin, hygromycin, or zeocin, among others), cloned by colony formation or limiting dilution, and clones expressing the unselected markers of interest are identified using various methods, including RNA dot blot assays, lectin staining assays, or functional assays. This general approach was first described in 1990 (Jarvis, D. L., Fleming, J. G. W., Kovacs, G. R., Summers, M. D. and Guarino, L. A. 1990. Use of early baculovirus promoters for continuous expression and efficient processing of foreign gene products in stably-transformed lepidopteran cells. Bio/Technology 8:950-955) and has been reviewed recently (Harrison, R. L. and Jarvis, D. L. 2006. Transforming lepidopteran insect cells for improved protein processing. In D. W. Murhammer (ed.), Methods in Molecular Biology: Baculovirus Expression Protocols. Humana Press, Clifton, N.J.; in press).

Methods for generating transgenic insects are conventional. For example, in one embodiment, one or more genes to be introduced are placed under the control of a suitable expression control sequence, and are cloned into a vector, such as a viral vector (e.g., an attenuated baculovirus vector, or a non-permissive viral vector that is not infective for the particular insect of interest). The sequences to be introduced into the insect are flanked by genomic sequences from the insect. The construct is then introduced into an insect egg (e.g., by microinjection), and the transgene (s) then integrate by homologous recombination of the flanking sequences into comparable sequences in the insect genome.

In another embodiment, the vector is a transposase-based vector. One form of such transposase-based vectors is a viral vector (such as those described above) that further comprises inverted terminal repeats of a suitable transposon, between which the transgene of interest is cloned. One or more genes of interest, under the control of a suitable expression control sequence (s), are cloned into the transposon-based vector. In some systems, the transposon based vector carries its own transposase. However, generally, the transposon based vector does not encode a suitable transposase. In this case, the vector is co-infected into an insect (e.g., an insect larva) with a helper virus or plasmid that provides a transposase. The recombinant vector (along with, generally, a helper) is introduced by conventional methods (such as microinjection) into an egg or early embryo; and the transgene (s) become integrated at a transposon site (such as sequences corresponding the inverted terminal repeat of the transposon) in the insect genome.

Suitable types of transposon-based vectors will be evident to the skilled worker. These include, e.g., Minos, mariner, Hermes, Sleeping Beauty®, and piggyBac.

In a preferred embodiment, the vector is a "piggyBac" vector. The TTAA-specific, short repeat elements are a group of transposons (Class II mobile elements) that have similar structures and movement properties. A typical piggyBac vector (formerly IFP2) is the most extensively studied of these insertion elements. PiggyBac is 2.4 kb long and terminates in 13 bp perfect inverted repeats, with additional internal 19 bp inverted repeats located asymmetrically with respect to the ends (Cary et al. (1989) Virology. 172, 156-69). A piggyBac vector may encode a trans-acting transposase that facilitates its own movement; alternatively, these sequences can be deleted and this function can be supplied on a helper plasmid or virus. piggyBac has been deleted for non-essential genes, into which large inserts can be cloned. Inserts as large as about 15 kB can be cloned into certain piggyBac vectors. This allows, for example, for the insertion of about six or seven genes with their expression control sequences. Thus, a collection of glycosylation enzymes, marker proteins, or the like, can be introduced together via a single transposon vector, into a single site in an insect genome.

Several piggyBac vectors have been developed for insect transgenesis. Two particularly useful constructs, defined as minimal constructs for the movement of piggyBac vectored sequences, were developed by analysis of deletion mutations both within and outside of the boundaries of the transposon (Li et al. (2001) Mol. Genet. Genomics. 266, 190-8). Using constructs such as these it is possible to increase the amount of genetic material mobilized by the piggybac transposase by minimizing the size of the vector. The minimal requirements for movement include the 5' and 3' terminal repeat domains and attendant TTAA target sequences.

Nearly all of the internal domain may be removed, although more recent data indicates that some of this region may be required for efficient translocation of the mobilized sequences into the genome of the insect. In addition, a minimum of 50 bases separating the TTAA target sites of the element is required for efficient mobilization (Li et al. (2001), supra). PiggyBac can transpose in insect, cells while carrying a marker gene, and movement of the piggyBac element can occur in cells from lepidopteran species distantly related to the species from which it originated. PiggyBac has been shown to transform *D. melanogaster*, the Carribean fruit fly, *Anastrepha suspena*, the oriental fruit fly, *Bactrocera dorsalis, Bombyx mori, Pectinophora glossypiella, Tribolium castellani*, and several mosquito species. At least three lepidopteran species, *P. gossypiella, T. ni* and *B. mori*, have been successfully transformed by the piggyBac element.

Generally, a helper virus or plasmid that expresses a transposase is co-introduced with the transposon-based vector as above. Expression of the transposase is determined by the choice of promoter for the insect system being tested. Toward that end, the present inventors have constructed several promoter-driven helper constructs that are useful for lepidopteran transformation, including the *Drosophila* hsp70, baculovirus iel promoter, and *Drosophila* Actin 5C promoter. Of these helper constructs, the hsp70 promoted helper, is particularly useful and serves as the primary helper for the transgenesis experiments in the Examples.

For further guidance on the use of baculovirus-based vectors, see, e.g., WO01/29204 and U.S. Pat. No. 6,551,825. Other recent references that discuss piggyBac vectors and methods for generating transgenic insects using them include, e.g., Handler et al. (1998) Proc Natl Acad Sci 95, 7520-7525; Fraser, M. J (2001) The TTAA-specific family of transposable elements. In: Insect transgenesis: Methods and Applications. A. A. James and A. H. Handler, eds. CRC Press, Orlando, Fla.; Lobo et al. (1999) Mol. Gen. Genetics 261, 803-810; Grossman et al. (2000) Insect Biochem. Mol. Biol. 30, 909-914; Lobo et al. (2001) Mol. Gen. Genom. 265, 66-71; Lorenzen et al. (2003) Insect Mol. Biol. 12, 433-40; Hacker et al. (2003) Proc Natl Acad Sci USA. 100, 7720-5; Sumitani et al. (2003) Insect Biochem Mol. Biol. 33, 449-58; Horn et al. (2003) Genetics 163 647-61; and Tomita et al. (2003) Nat. Biotechnol. 21, 52-6.

Methods for introducing constructs into an embryo to generate a transgenic insect (e.g., by microinjection) are conventional. Survivorship is usually quite high (up to 75%) for microinjected embryos. In general, preblastoderm eggs are stuck with a fine glass capillary holding a solution of the plasmid DNA and/or the recombinant virus. $G_O$ larvae hatched from the virus-injected eggs are then screened for expression of the gene of interest. Breeding transgenic $G_1$s with normal insects results in Mendelian inheritance.

Once a transgene (s) is stably integrated into the genome of an insect egg or early embryo, conventional methods can be used to generate a transgenic insect, in which the transgene (s) is present in all of the insect somatic and germ cells. When a subset of the complete set of glycosylation enzymes is present in a transgenic insect, other transposon-based vectors, which express different subsets of the glycosylation genes, can be introduced sequentially into the insect genome, and transgenic insects can then be generated. In another embodiment, when different subsets of the complete set of glycosylation enzymes are present in two or more individual transgenic insects, these insects can be genetically crossed to produce a transgenic insect that expresses a larger subset, or a complete set, of the glycosylation enzyme genes.

In some embodiments, the transgenic insects are heterozygous for the modifying enzyme genes. For example, when potentially toxic glycosylation enzymes are produced constitutively, it may be advantageous for the insects to be heterozygous, to limit the amount of the enzyme that is produced. In other embodiments, the insects are homozygous for the transgenes. Methods for producing homozygous transgenic insects (e.g., using suitable back-crosses) are conventional.

Another embodiment of the invention is an isolated cell, or progeny thereof, derived from a transgenic insect of the invention. Suitable cells include isolated germ line cells, and cells that can be used for the in vitro production of a polypeptide exhibiting a partial or complete pattern of mammalian glycosylation. Methods for obtaining and propagating cells from a transgenic insect, and using them (e.g. to generate more insects, or to generate glycosylated proteins) are conventional.

The transgenic insects discussed above can be used to produce polypeptides of interest that exhibit partial or complete patterns of mammalian glycosylation. For example, the insects can be used in methods for glycosylating polypeptides in a mammalian (human) glycosylation pattern.

One embodiment of the invention is a method for producing, in an insect, a mammalianized (e.g., humanized) glycosylated form of a polypeptide of interest that is endogenous to the insect. The method comprises cultivating (culturing, rearing) a transgenic insect as discussed above (preferably in the form of a larva) under conditions effective to produce a mammalianized glycosylated form of said polypeptide of interest. Conditions for cultivating insects, such as insect larvae, are conventional.

Another embodiment of the invention is a method for producing, in an insect (preferably an insect larva), a mammalianized (e.g., humanized) glycosylated recombinant polypeptide containing sulfated complex N-glycan residues. In embodiments of the invention, the recombinant polypeptide is an endogenous insect protein or, preferably, it is a heterologous protein. In one embodiment, this method comprises introducing into a transgenic insect cell or insect (the latter preferably in the form of a larva) a construct comprising nucleic acid encoding said recombinant protein, operably linked to an expression control sequence. In a preferred embodiment, these sequences are cloned into a suitable viral vector (such as a baculovirus-based vector, entomopox-based vector, or others). The coding sequences may be operably linked to an expression control sequence from the virus, itself, or to another suitable expression control sequence. Suitable virus-based vectors include, e.g., baculovirus vectors (such as vectors based on *Autographa californica* NPV, *Orgyia pseudotsugata* NPV, *Lymantria dispar* NPV, *Bombyx mori* NPV, *Rachoplusia ou* NPV, *Spodoptera exigua* NPV, *Heliothis zea* NPV, *Galleria mellonella* NPV, *Anagrapha falcifera* nucleopolyhedrovirus (AfNPV), *Trichoplusia ni* singlenucleopolyhedrovirus (TnSNPV)); retroviral vectors; and viral vectors that comprise transposon recognition sequences (e.g., piggyBac vectors); etc. As discussed above, baculovirus-based vectors have been generated (or can be generated without undue experimentation) that allow the cloning of large numbers of inserts, at any of a variety of cloning sites in the viral vector. Thus, more than one heterologous polypeptide may be introduced together into a transgenic insect cell or insect of the invention. The viral vector can be introduced into an insect cell or insect by conventional methods, such as by in vitro inoculation (insect cells) or oral ingestion (insect larvae).

In one embodiment, the baculovirus replicates until the host insect is killed. The insect cell or insect lives long enough to produce large amounts of the glycosylated polypeptide of interest. In another embodiment, a baculovirus is used that is attenuated or non-permissive for the host. In this case, the host is not killed by replication of the baculovirus, itself (although the host may be damaged by the expression of the glycosylation enzymes and/or the heterologous protein of interest).

In another embodiment, sequences encoding one or more recombinant proteins of interest, operably linked to an expression control sequence, are cloned into a suitable transposon-based vector (such as a piggyBac vector). Like the baculovirus vectors discussed above, transposon-based vectors can carry large inserts, so more than one heterologous polypeptide may be introduced together into a transgenic insect of the invention. Transposon-based vectors may on occasion insert into the DNA of somatic cells, and thus be stably expressed for relatively long periods of time.

In another embodiment, sequences encoding one or more recombinant proteins of interest, operably linked to an expression control sequence, are cloned into a retrovirus vector, or any other suitable virus vector. Such a construct may insert into the DNA of somatic cells, and thus be stably expressed for relatively long periods of time.

The genetically engineered insect cells, insects, and kits of the instant invention comprise at least one nucleic acid encoding at least one modifying enzymes involved in the glycosylation pathway. In a particular embodiment, the insect cells, insects, and kits comprise at least one nucleic acid encoding at least one, at least two, at least three, at least four, at least five, at least six, or all seven of the following modifying enzymes: i) —N-acetylglucosaminyltransferase II, ii) —N-acetylglucosaminyltransferase III, iii) —N-acetylglucosaminyltransferase IV, iv) —Beta 1,4-Galactosyltransferase, v) —N-acetylglucosamine-6-O-sulfotransferase, vi) -Galactose-3-O-sulfotransferase, and vii) —N-acetylglucosaminyltransferase V. The cells, insects, and kits may also comprise a combination of modifying enzymes, for example, wherein the combination is selected from the group of aforementioned enzymes listed in this paragraph, consisting of the combinations: enzymes i), iv) and v), enzymes i), iv) and vi), enzymes i), iv), v), and vi), enzymes i), ii), iv), and v), enzymes i), ii), iv) and vi), enzymes i), ii), iv), v) and vi), enzymes i), iii), iv), and v), enzymes i), iii), iv), vi), enzymes i), iii), iv), v), vi), enzymes i), iii), v), and vii), enzymes i), iii), iv), vi), and vii), and enzymes i), iii), iv), v), vi), and vii).

The insect cells, insects, and kits may further comprise —N-acetylglucosaminyltransferase I. In a particular embodiment, the insect cells may comprise —N-acetylglucosaminyltransferase II, -Beta 1,4-Galactosyltransferase, —N-acetylglucosamine-6-O-sulfotransferase, and -Galactose-3-O-sulfotransferase.

In another embodiment of the invention, the insect cells, insects, and kits may further comprise at least one of the following modifying enzymes: alpha 2,3-sialyltransferase, alpha 2,6-sialyltransferase. In yet a further embodiment, the insect cells, insects, and kits may comprise a sulfate transporter. In an additional embodiment, the cells, insects, and kits further comprise at least one, at least two, or all three of the enzymes sialic acid synthase (SAS), CMP-sialic acid synthetase (CMP-SAS), and a CMP-SAS transporter.

As mentioned above, the nucleic acids encoding these enzymes may be expressed in constitutive or regulated fashion. Established methods can be employed to characterize multiple clones to identify transgenic insect cell line(s) capable of producing complex N-glycans with a variety of different structures including, but not limited to, biantennary, terminally galactosylated structures with or without bisecting N-acetylglucosamine residues, triantennary, terminally galactosylated structures, tetraantennary, terminally galactosylated structures, and any of the preceding structures with 6-O-sulfation of the peripheral N-acetylglucsoamine residues and/or 3-O-sulfation of the peripheral galactose residues.

In the case of some, but not all glycoproteins, the glycans will require terminal sialylation. Methods of characterizing the enzymes may include, but are not limited to: Lectin-based histochemical staining; PCR; Southern blotting analysis; RNA dot blot analysis; Northern blotting analysis; RT-PCR analysis; Enzyme activity assays; Lectin blotting analysis; Cell growth curves and maximal density analyses.

In another embodiment, the kits can also contain an insect cell or cell line and at least one nucleic acid encoding at least one protein of interest. In this regard, the kit can be used to provide sulfated complex N-glycans on proteins that are either endogenous or exogenous to the cell. The kits can further comprise instructional materials, containers, and buffers.

The following examples are provided to illustrate certain embodiments of the invention. They are not intended to limit the invention in any way.

Example I

Creation of Transgenic Insect Cell Lines Expressing Glycosylation Enzymes of Interest In the present example, insect cells will be created which express mammalian genes that will allow them to produce rHA's with more authentic N-glycans. Thus, ExpresSf+® cells will be transformed with six mammalian genes encoding four glycosyltransferases and two sulfotransferases.

Three dual piggyBac vectors that can provide efficient transfer and balanced expression of foreign gene pairs (42) will be used for this purpose. The first will encode Gn-TII and Gal-T, the second will encode Gn-TIII and Gn-TIV, and the third will encode Gn6ST and Gal3ST. We have already constructed and functionally characterized a dual piggyBac vector encoding the Gn-TII/Gal-T gene pair (42). Dual piggyBac vectors encoding the two other gene pairs will be constructed using IE plasmid and dual piggyBac vector precursors that are available. Briefly, PCR will be used to produce DNA copies of the human Gn-TIII (Acc #NM002409), Gn-TIV-A (Acc #NM012214), Gn6ST (Acc. # AB014679) and Gal3ST2 (Acc. #NM022134) open reading frames, while incorporating appropriate unique restriction sites onto their ends. The resulting products will be gel-purified and cloned into pCR-TOPO2.1 (Invitrogen). Error-free recombinants will be identified by restriction mapping and sequencing, and then the inserts will be excised using the unique restriction sites, gel-purified, and subcloned into the corresponding sites in our dual piggyBac vector precursors. This will yield two new dual piggyBac vectors encoding Gn-TIII/Gn-TIV and Gn6ST/Gal3ST2, which will be checked by restriction mapping and purified from scaled-up E. coli cultures. Each new vector or the empty piggyBac vector precursor (control) will then be used to transfect ExpresSf+® cells for functional assays. The cells will be extracted 24 h later and assayed for the relevant Gn-T activities, as described previously (45). Briefly, these assays will involve incubating samples of the extracts containing equal amounts of total protein with fluorescently labeled N-glycan acceptor and UDP-GlcNAc donor substrates, then resolving the partially purified N-glycans using an established reverse phase HPLC method to assess product formation. Alternatively, microsomes will be isolated from the transfected cells and assayed for the relevant sulfotransferase activities, as described previously (26, 43). Briefly, these assays will involve incubating samples of the microsomes containing equal amounts of total protein with 3'-phosphadenosine 5'-phospho[$^{35}$S]sulfate and N-acetyllactosamine, then separating the reaction products using an established TLC method. Fluorography will be performed on the TLC plates to assess product formation.

All three dual piggybac vectors will be used to transform these cells. The vectors will be mixed with a helper plasmid encoding the piggyBac transposase and an IE expression plasmid encoding a hygromycin resistance gene, both of which are available. ExpresSf9+ cells will then be transfected with this mixture or with the same mixture lacking the selectable marker as a control for the selection process. One day later, the transfected cells will be selected with hygromycin and cloned, as described previously (11, 21). Surviving clones will be expanded and screened by staining with fluorescein-tagged *Erythrina cristagalli* lectin (ECL), which binds to terminal galactose-β1,4-N-acetylglucosamine residues. This will be the terminal disaccharide found on N-glycans produced by any transformed expresSf9+ subclone expressing the mammalian Gn-TII/Gal-T gene pair, which is prerequisite for any insect cell line to be able to produce a humanized form of rHA. Importantly, this is a relatively fast and easy screen that can be performed in a 96 well plate format to identify expresSf9+ clones with this minimal capability. Furthermore, we recently used this same approach with another lectin to isolate a transgenic Sf9 subclone encoding six mammalian protein N-glycosylation functions transposed using three piggyBac vectors. 137 antibiotic-resistant transformants were tested and 14 clones expressing all six genes were obtained, for an efficiency of ~10%. ECL-positive clones will be further screened to determine if they express the other four mammalian genes. The usual approach is to perform RNA dot blots for this purpose because it, too, is relatively fast and easy and can be performed in a 96 well plate format. Another option will be to use an antiserum specific for bisecting N-acetylglucosamine to identify clones producing N-glycans with bisected structures (32). Once these screens are complete, potentially useful ExpresSf+® subclones will be expanded and cell banks prepared. The presence of each of the relevant glycosyltransferase and sulfotransferase activities will be examined more precisely and directly using triplicate samples of extracts or microsomes containing equal amounts of total protein. The Gn-TIII, Gn-TIII, Gn6ST, and Gal3 ST assays will be performed as described above and the Gn-TII and Gal-T assays will be performed using well established methods, which have been described in previous publications (12-15, 20, 22, 41, 46). All results will be presented as enzyme activity units/h/mg of total protein, with background activities (boiled homogenates) subtracted from the experimental values and endogenous activities measured in the negative controls presented as such, to show the levels of each activity, if any, in the parental insect cell line.

This work will yield at least one transgenic subclone of ExpresSf+® cells that can produce rHA's with complex, biantennary, terminally galactosylated N-glycans. It will yield additional subclones that can produce bisected N-glycans of this type and/or triantennary, terminally galactosylated N-glycans, and/or complex, biantennary, terminally galactosylated N-glycans with sulfated N-acetylglucosamine and galactose residues.

Production of FluBlØk® in the Parental and Transgenic Insect Cell Lines

Parental and transgenic ExpresSf+® cells will be infected with a recombinant baculovirus encoding the HA from a potentially pandemic H5N1 strain of avian influenza virus. This baculovirus has been constructed and virus banks have been prepared by Protein Sciences. As mentioned above, Protein Sciences has extensive experience producing and purifying rHA using the BEVS at various levels, including the 500 L level. Preliminary experiments will be conducted to compare rHA expression levels in the parental and transgenic ExpresSf+® cells. Each cell type will be infected with the recombinant baculovirus and then rHA expression levels will be examined at various times after infection by SDS-PAGE and western blotting analysis. rHA activity will be examined at various times after infection by measuring hemagglutination of chicken red blood cells. Finally, rHA production will be assayed using a serial radial immunodiffusion assay (SRID), which is the FDA standard for determining influenza vaccine potency. Once these preliminary comparisons are complete, lab scale production work designed to yield a minimum of ~10 mg of purified rHA from each relevant cell type for subsequent biochemical and immunological analyses can be performed. The different forms of rHA produced by various cell lines will then be purified from the parental ExpresSf+® cell line. The BEVS-produced rHA's will be transported to the insect cell surface, extracted by detergent lysis, and the extracts will be clarified to remove large cellular debris prior to chromatography. Purification for rHA's entails two ion exchange steps and a hydrophobic interaction chromatography step. However, the conditions needed to ensure the success of this purification process suggest that rHA glycosylation and/or folding might be important. An alternative approach entails engineering the influenza HA gene to encode a 6×HIS tag and this tag will be used as the basis for affinity purification of the rHA's produced by any one of our insect cell lines. This will allow direct comparisons of these products and will also allow us to identify any differences in the behavior of these proteins, as compared to previous batches of the H5 rHA protein.

The structures of the N-glycans on FluBlØk® produced by both insect cell lines will then be characterized. Metabolic labeling with [$^{35}$S]sulfate and lectin blotting analyses will be used as fast and simple ways to obtain preliminary structural information. These structures will be analyzed using more tedious and complex HPLC and mass spectroscopic methods, but these will provide more direct and definitive structural information.

To obtain a preliminary view of the ability of relevant transgenic ExpresSf+® subclones to sulfate rHA, parental or transgenic cells will be infected with the recombinant baculovirus encoding H5 rHA and then radiolabeled with 1 mCi/mL of [$^{35}$S]sulfate from 20-24 h postinfection. The rHA will then be extracted, immunoprecipitated, treated with buffer or PNGase-F, and analyzed by SDS-PAGE and autoradiography, as described previously (23). The results will reveal whether or not the radioactive sulfate was specifically incorporated into the N-glycans of the rHA produced by the transgenic insect cell line.

To obtain a preliminary view of the carbohydrate compositions of the rHA's produced by the parental and transgenic insect cells, lectin blotting assays will be performed. Equal amounts of the rHA's will be purified from these cells as described above and then treated with buffer alone, PNGase-F, or β-galactosidase. The reaction products will be resolved by SDS-PAGE, transferred to a membrane, and probed with biotinylated ECL, which binds to terminal galactose-β1,4-N-acetylglucosamine residues, as noted above. ECL binding will be detected using alkaline phosphatase-conjugated streptavidin. Inclusion of the endo- and exoglycosidase treated samples and the untreated rHA from the parental cell line are critical controls that will allow us to monitor the specificity of lectin binding (4, 13-15, 19, 20, 41) and has validated their lectin blotting method using more direct and sophisticated methods, including HPLC and mass spectroscopy (1, 13, 14, 52).

In preparation for HPLC and mass spectroscopic analyses, the N glycans must be removed and recovered from the purified rHA's. The starting material will be the rHA's purified from the parental or transgenic ExpresSf+® cells, as described above. Past experience suggests we will need about 1 mg of each purified recombinant glycoprotein from each cell type for comprehensive N glycan structural analyses. Thus, 1 mg samples of the recombinant glycoproteins from each source will be denatured and exhaustively digested with PNGase-F, as described previously (13). The released N glycans will be bound to graphitized carbon cartridges, the proteins and salts will be washed away with water, and total N-glycans will be eluted with acetonitrile. Alternatively, we will use trifluoroacetic acid to separately elute the neutral and charged (sulfated) N glycans for independent analyses (39). After being eluted, the N glycans will be analyzed by HPLC and/or mass spectroscopy, as described below.

The HPLC method to be used for the N glycan structural analyses will be high pH anion exchange chromatography with pulsed amperometric detection (HPAEC-PAD; (9, 4, 13, 14). N glycans isolated as described above will be injected into a Dionex HPAEC-PAD system equipped with a Carbo-Pac PA100 column equilibrated with 50 mM NaOH, which is designed for oligosaccharide separations. After being injected, the column will be washed with 50 mM NaOH, then the N glycans will be eluted with a linear gradient of 0 to 125 mM sodium acetate over 45 minutes at a flow rate of 1 ml/min. Commercial N glycans will be used as standards and the structures of the N glycans isolated from the rHA's produced by the parental or transgenic ExpresSf+® cells will be presumptively identified by co-elution with these standards. Further information will be obtained by treating the PNGase-released N-glycans with exoglycosidases (17). For example, if the released N glycans are treated with β-galactosidase and the profile changes in the predicted way, this will indicate that the original N glycan was terminally galactosylated. Many specific exoglycosidases are commercially available, including β-galactosidases, α fucosidases, β N acetylhexosaminidases, and α-mannosidases, and they can be applied to effectively sequence N glycans (17). Together with the HPLC analyses of the PNGase-F-released glycans, analysis of the exoglycosidase-treated N glycans will allow for the identification of their structures with great confidence.

However, a more direct and unequivocal determination of N glycan structure will be obtained by using mass spectroscopy. MALDI-TOF and tandem mass spectroscopic analyses of N glycans will be employed.

The immune responses induced by FluBlØk® produced by both insect cell lines will be characterized. The immune response induced by the purified H5 rHA antigens produced will be assessed through rat immunization studies. Three different treatment groups will be included in this study. Each group will consist of 10 male and 10 female Sprague-Dawley rats. One will be immunized with saline, another with the rHA produced by the parental ExpresSf+® cell line, and the third with the rHA produced by a selected transgenic version of the ExpresSf+® cell line, as outlined in Table 1.

TABLE 1

Immunogenicity and Safety Animal Study Design

| Group | Treatment | Dose (μg rHA) | Immunization Schedule | Animals/Group |
|---|---|---|---|---|
| 1 | Saline Control | 0 | Day 1, Day 15 | 10M/10F |
| 2 | Parental H5 rHA | 90 | Day 1, Day 15 | 10M/10F |
| 3 | Transgenic H5 rHA | 90 | Day 1, Day 15 | 10M/10F |

The detailed animal study protocol will call for two immunizations (90 μg each) with the rHA purified from either the parental or the transgenic insect cells. Animals will be injected intramuscularly in the hind legs and the study will extend for a total of 45 days (30 days after last immunization). Animals will be bled via the orbital sinus and serum will be collected for analysis prior to each immunization, on study day 30, and at the conclusion of the study. Immunogenicity will be assessed by determining anti-rHA IgG titers by ELISA and also by determining hemagglutination inhibition (HAI) titers using the rHA in conjunction with chicken red blood cells. Safety will be assessed by monitoring body-weight, food consumption, and by clinical observation, as well as by harvesting tissues for histopathologic examination and determining organ weights at the end of the study. This study was designed to utilize dosages and treatment schedules appropriate to generate the initial immunogenicity and safety data needed to support a downstream IND application for the potential clinical evaluation of either vaccine candidate.

The following materials and methods are provided to facilitate the practice of this invention.

Figure 1B:
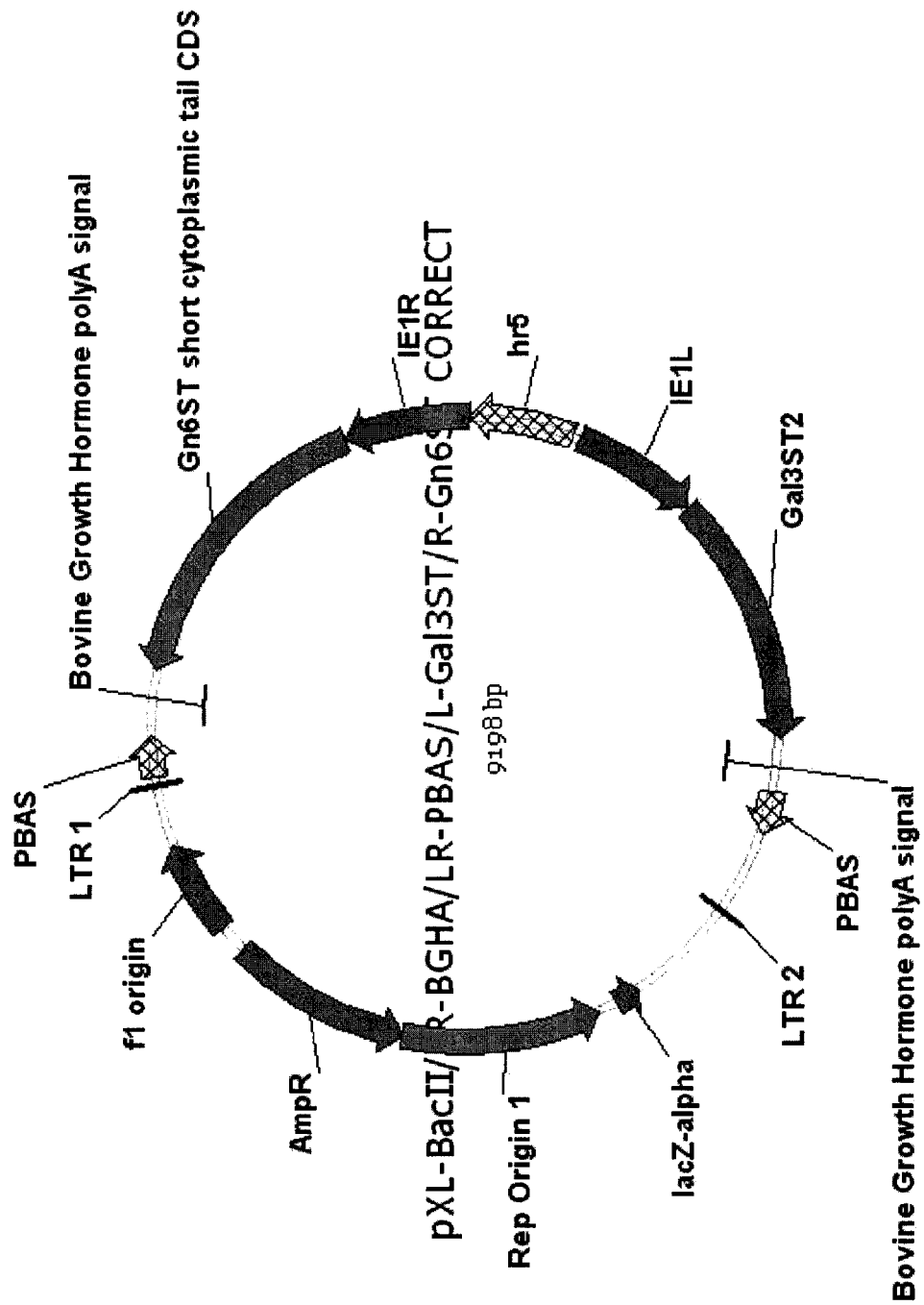
FIG. 1B is a map of the resulting plasmid.

FIG. 1 is a schematic diagram depicting the construction of pBac vector encoding Gal3ST/Gn6ST genes. Briefly, this was done as follows:

1. Amplify BGHA using the following primers by PCR;

```
Sense:
                                              (SEQ ID NO: 1)
5'-GGTACCGTTTAAACGGATCCACTAGTGGGCCCGCCTCGACTG TGCCTTCTAG-3'
   Kpn I    Pme I    BamH I    Spe I    Apa I Antisense:
                                              (SEQ ID NO: 2)
5'AAGCTTATAACGTCTAGAGTTAACGTCGACTCCCCAGCATGCCTGCTA TTG3'
  Hind III        Xba I    Hpa I   Sal I
```

Once amplified clone into PCR2.1-TOPO to produce pCR2.1TOPOBGHA-HpaI. See FIG. 1.

2. Digest by Hind III/Kpn I from pCR2.1TOPOBGHA-HpaI and insert the fragment into pDIE1-TOPO.3 as shown in the power point figure to produce pDIE1-TOPO3/KpnI-LR-BGHA-HpaI/HindIII.

3. Use the following primers to amplify the Gn6ST (short form) cDNA and clone it into PCR2.1-TOPO to produce pCR2.1-TOPO/NruI-Gn6ST-NotI;

```
    f-Gn6ST (Tm = 63.1° C.; Length = 21),
    5'-TCGCGAATGAAGGTGTTCCGT-3'      (SEQ ID NO: 3)
       NruI r-Gn6ST (Tm = 72.3° C.; Length = 23),
    5'-GCGGCCGCTTAGAGACGGGGCTT-3'    (SEQ ID NO: 4)
       NotI
```

The resulting sequence will be confirmed by restriction enzyme analysis and DNA sequence analysis. Digest the PCR2.1-TOPO/NruI-Gn6ST-NotI by Nru I/Not I and religate the fragment into pDIE1-TOPO3/KpnI-LR-BGHA-HpaI/HindIII as shown in FIG. 1 to produce pDIE1-TOPO3/LR-BGHA-R-Gn6ST.

The following primers will be used to amplify the Gal3ST cDNA and TOPO clone it into PCR2.1-TOPO to produce pCR2.1 TOPO-KpnI-Gal3 ST-PmeI;

```
f-Gal3ST (Tm = 61° C.; Length = 21),
5'-GGTACCATGATGTCCTTGCTG-3'          (SEQ ID NO: 5)
   KpnI r-Gal3ST (Tm = 63° C.; Length = 24),
5'-GTTTAAACCTACGCCCCCAGGAAC-3'       (SEQ ID NO: 6)
   PmeI
```

The sequence will then be confirmed by restriction enzyme analysis and DNA sequence analysis. Digest pCR2.1TOPO-KpnI-Gal3ST-PmeI by Kpn I/Pme I and religate the fragment into pDIE1-TOPO3/LR-BGHA/R-Gn6ST as shown in FIG. 1 produce pDIE1/LR-BGHA/L-Gal3ST/R-Gn6ST.

Once both the cDNA Gal3ST/Gn6ST have been successfully inserted along with the poly A signal on the left side of the promoter IE-L the remaining task is to insert the piggyBac Activator sequence downstream of poly A signal. As shown in the figures below amplify the sequence using the following primers;

```
f-piggyBac Act Seq-Sal I (Tm = 56° C.;
Length = 21),
5'-GTCGACATGCGTAAAATTGAC-3'          (SEQ ID NO: 7)
   Sal I r-piggyBac Act Seq HpaI-XbaI (Tm = 57° C.;
Length = 27),
5'-GTTAACATTCGATAAAAGTTTTGTTAC-3'    (SEQ ID NO: 8)
   HpaI
```

Digest pCR2.1TOPO-PBAS-HpaI by Hpa I/Hind III and religate it into pDIE1/LR-BGHA/L-Gal3ST/R-Gn6ST at Sal I/Hind III to produce pDIE1/LR-BGHA-LR-PBAS/L-Gal3ST/R-Gn6ST.

Digest using Xba I and religate the cassette in pXLBac II at Xba I REs site. Screen for BOTH insert and orientation. Remember pXLBacII will donate one PBAS, while the pDIE1TOPO3/LR-BGHA/L-GnT4A/R-GnT3/LPBAS insert will donate the other. The PBAS from pXLBacII MUST, therefore, be positioned downstream of the Gn6ST gene.

Figure 2:
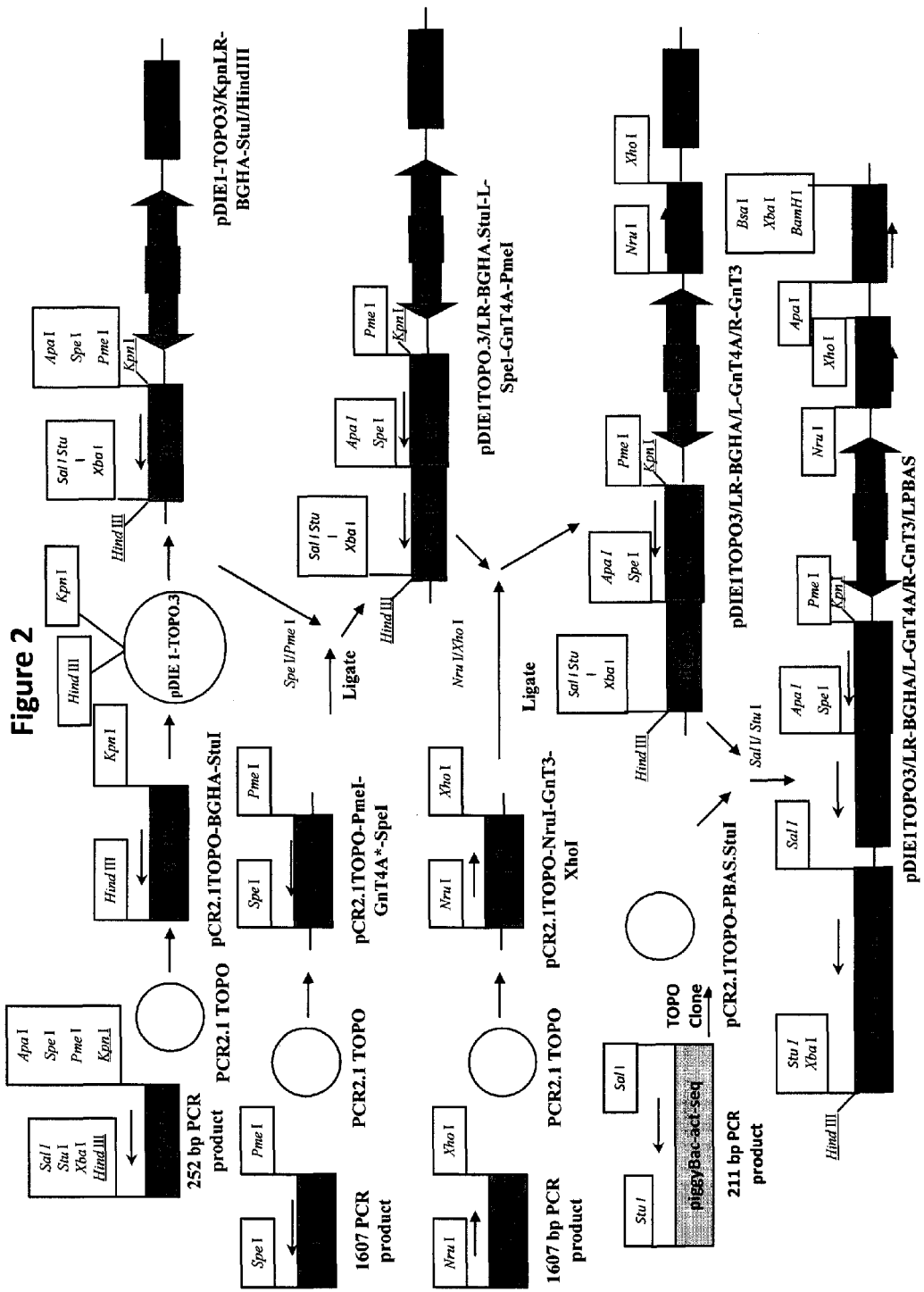
FIG. 2 is a schematic diagram depicting the construction of a dual piggyBac vector encoding the GnTIVA and GnTIII genes.
Figure 3A:
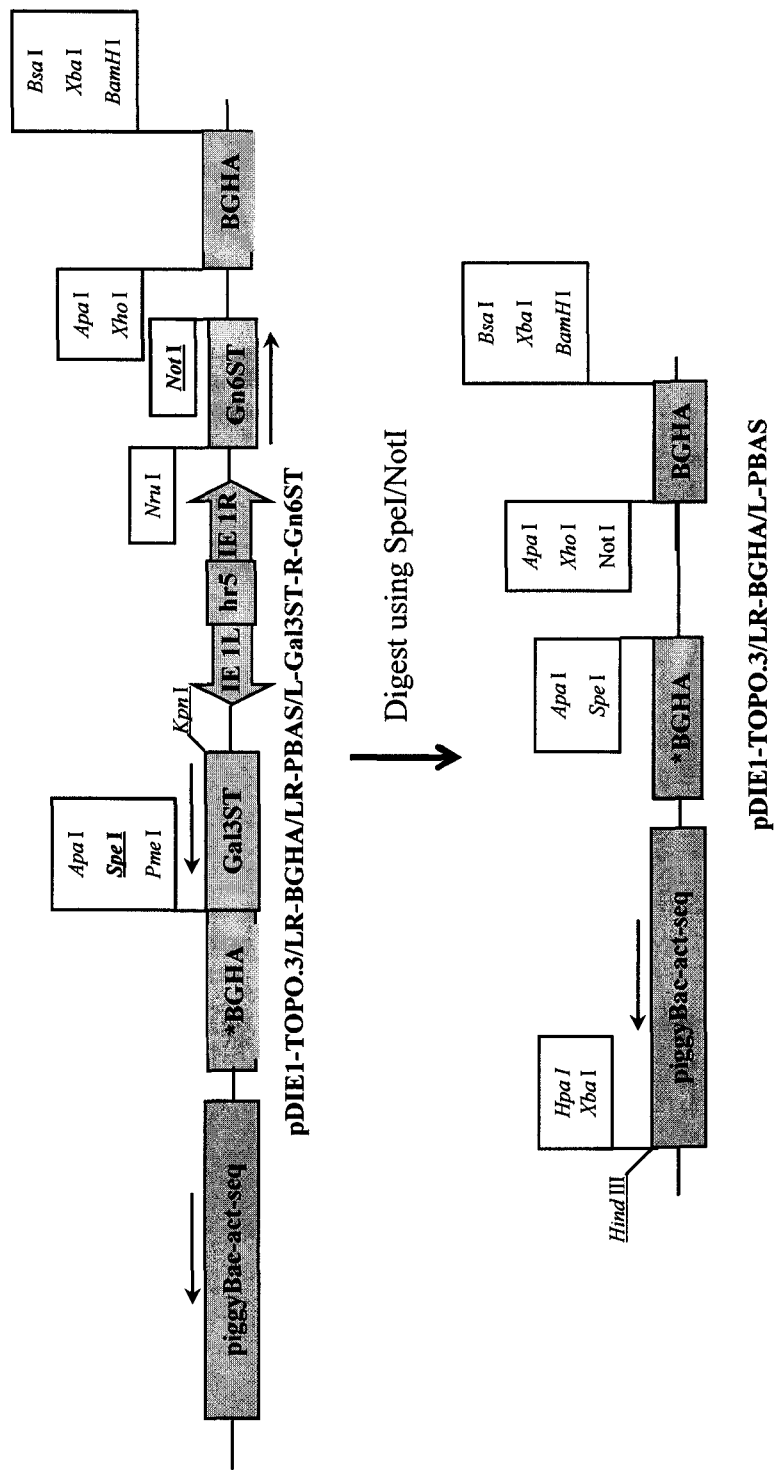
FIG. 3A shows the construction of pDIE1-TOPO.3/LR-BGHA/L-PBAS.
Figure 3B:
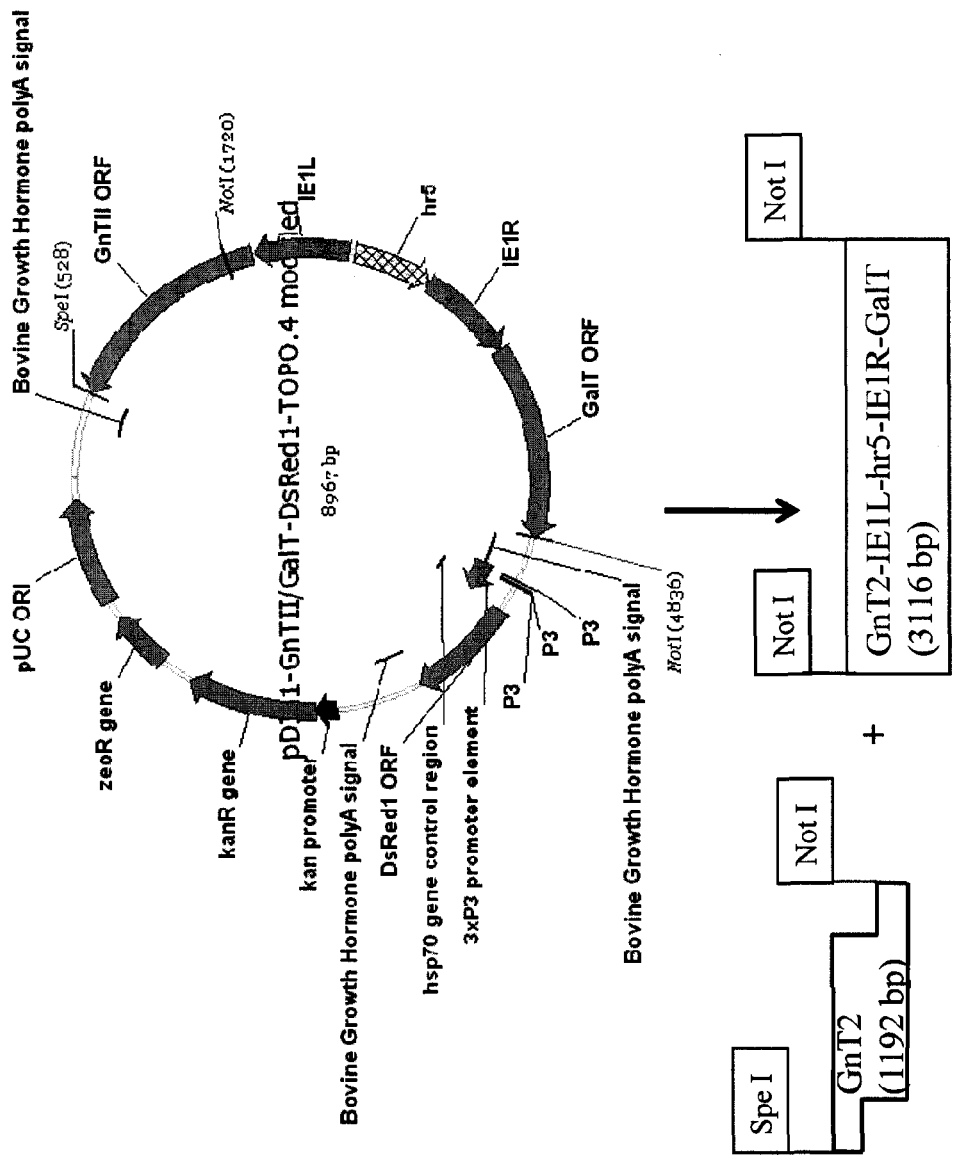
FIG. 3B shows a map of the plasmid utilized to prepare the GnT2 and GalT gene fragments.
Figure 3C:
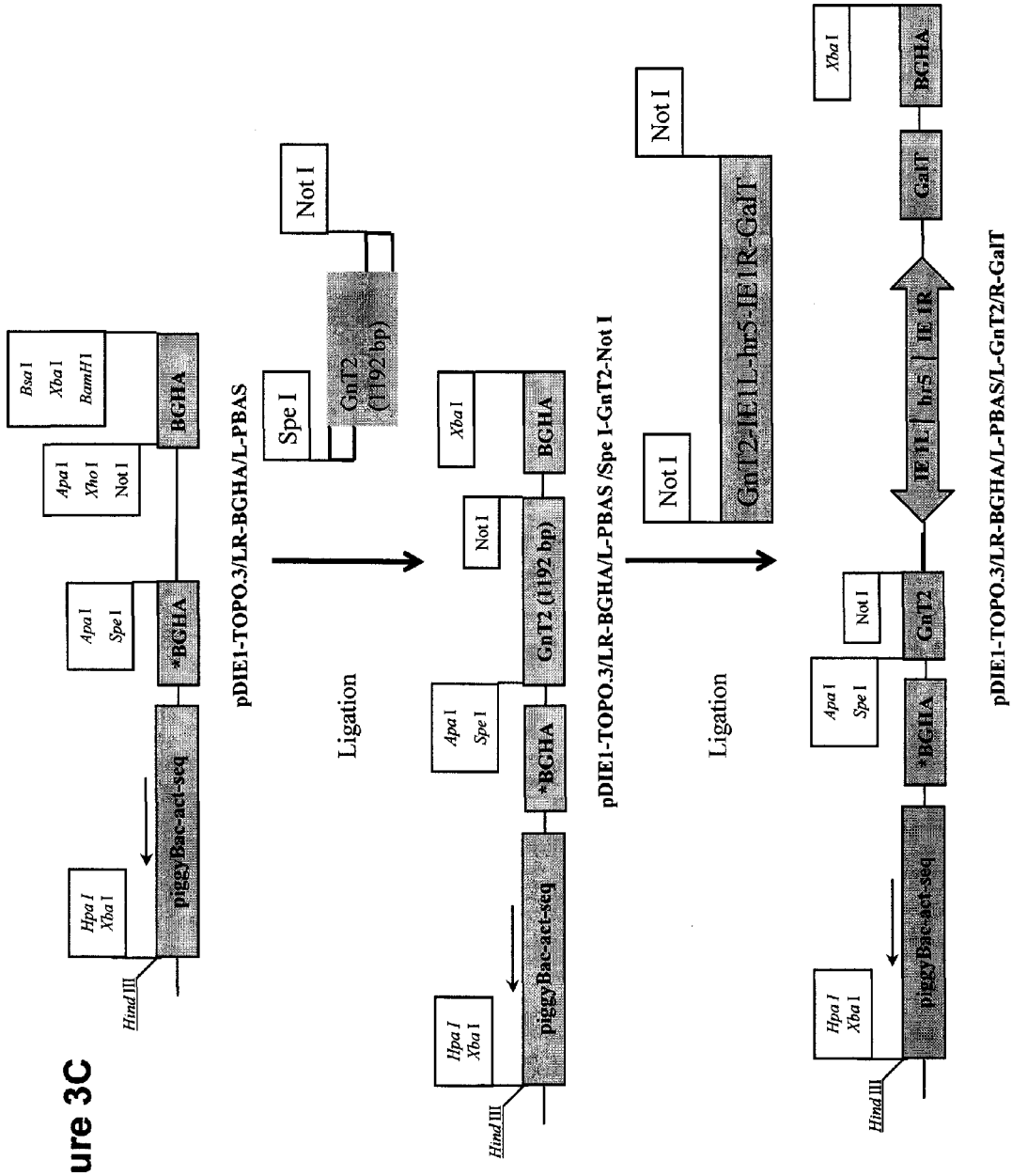
FIG. 3C is a schematic diagram depicting the construction of a dual piggyBac vector encoding the GnTII and GalT genes.
Figure 3D:
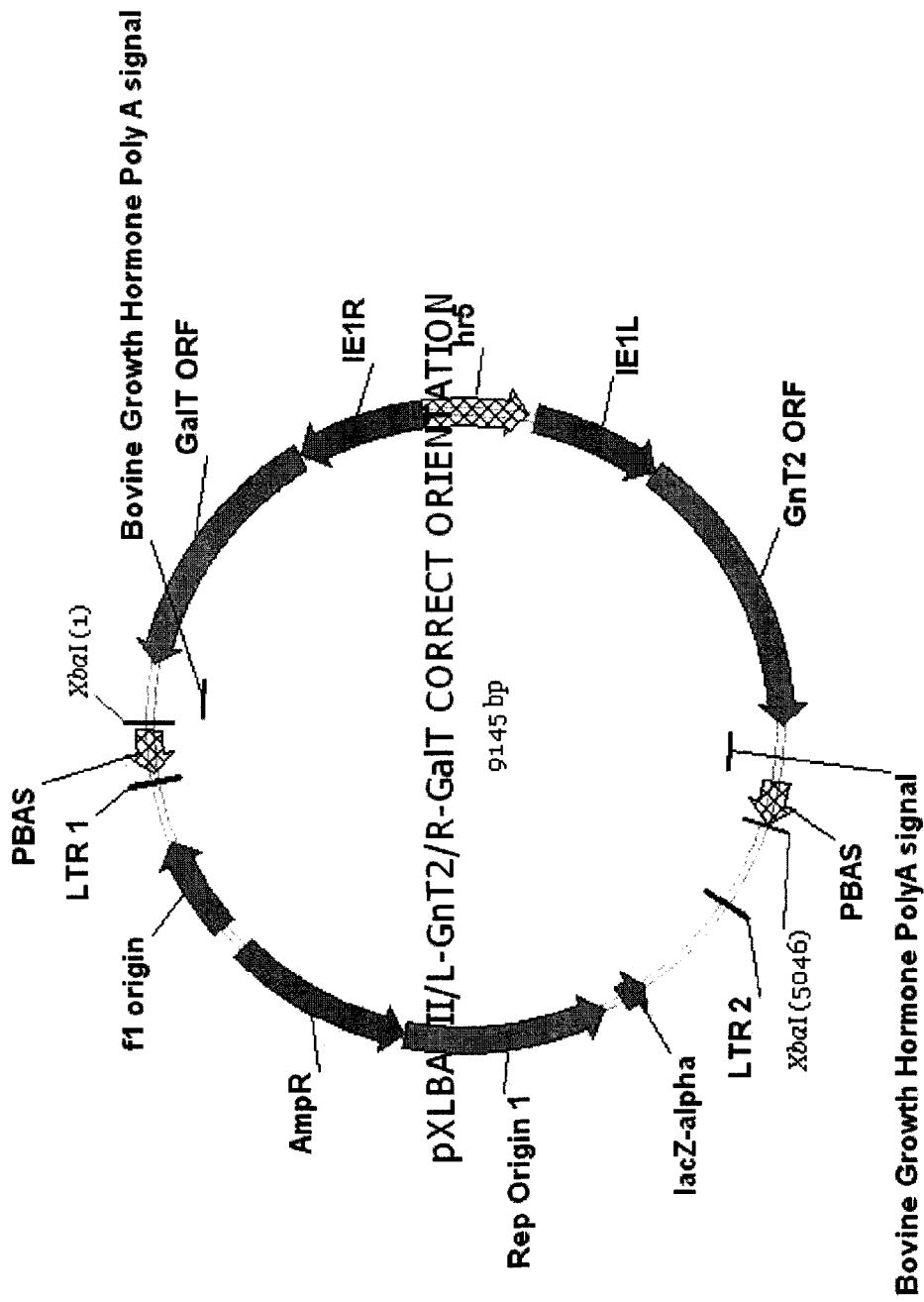
FIG. 3D is a map of the resulting plasmid.

FIG. 2 is a schematic diagram depicting construction of pBac vector encoding GnTIVA/GnTIII genes.

Briefly, BGHA was amplified using the following primers by PCR;

```
Sense:
                                              (SEQ ID NO: 1)
5'-GGTACCGTTTAAACGGATCCACTAGTGGGCCCGCCTCGACTG TGCCTTCTAG-3'
   Kpn I    Pme I    BamH I    Spe I    Apa I Antisense:
                                              (SEQ ID NO: 9)
5'-AAGCTTATAACGTCTAGAAGGCCTGTCGACTCCCCAGCATGCCTGCT ATTG-3'
   Hind III    Xba I    Stu I    Sal I
```

Once amplified TOPO clone it into PCR2.1-TOPO to produce pCR2.1TOPO-BGHA-StuI.

Digest by Hind III/Kpn I from pCR2.1TOPO-BGHA-StuI and insert the fragment into pDIE1-TOPO.3 as shown in FIG. 2 to produce pDIE1-TOPO3/KpnLR-BGHA-StuI/HindIII.

Amplify GnT4A cDNA and introduce a silent mutation at XbaI REs site. This allows the cloning of the cassette utilizing the Xba I in the dual vector. Use the following primers to amplify the cDNA and TOPO clone it into PCR2.1-TOPO to produce pCR2.1TOPO-PmeI-GnT4A*-SpeI (the * indicates GnTIVA gene has silent mutation that knocks out internal XbaI site, see FIG. 2):

```
f-GnT4A (Tm = 60.5° C.; Length = 24),
5'-GTTTAAACATGAGGCTCCGCAATG-3'       (SEQ ID NO: 10)
Pme I r-GnT4A (Tm = 57.2° C.; Length = 21),
5'-ACTAGTTCAGTTGGTGGCTTT-3'          (SEQ ID NO: 11)
   Spe I
```

Confirm the sequence by restriction enzyme analysis and DNA sequence analysis. Digest the pCR2.1TOPO-PmeI-GnT4A*-SpeI by Pme I/Spe I and religate the fragment into pDIE1-TOPO3/KpnLR-BGHA-StuI/HindIII as shown in FIG. 2 to produce pDIE1TOPO.3/LR-BGHA. StuI-L-SpeI-GnT4A-PmeI.

The following primers will be used to amplify the GnT3 cDNA and TOPO clone it into PCR2.1-TOPO to produce pCR2.1TOPO-NruI-GnT3-XhoI;

```
f-GnT3 (Tm = 61.8° C.; Length = 21),
5'-TCGCGAATGAGACGCTACAAG-3'        (SEQ ID NO: 12)
   Nru I r-GnT3 (Tm = 66.7° C.; Length = 22),
5'-CTCGAGCTAGACTTGCGCCTCG-3'       (SEQ ID NO: 13)
   Xho I
```

The sequence will be confirmed by restriction enzyme analysis and DNA sequence analysis. Digest the pCR2.1TOPO-NruI-GnT3-XhoI by Nru I/Xho I and religate the fragment into pDIE1TOPO.3/LR-BGHA.StuI-L-SpeI-GnT4A-PmeI as shown in the power point slide to produce pDIE1TOPO3/LR-BGHA/L-GnT4A/R-GnT3:

Once both the cDNA GnT4A/GnT3 have been successfully inserted along with the poly A signal on the left side of the promoter IE-L the remaining task is to insert the piggyBac Activator sequence. As shown in the figures below amplify the sequence using the following primers;

```
f-Sal I piggyBac Act seq (Tm = 60.7° C.;
Length = 21),
5'-GTCGACATGCGTAAAATTGAC-3'        (SEQ ID NO: 7)
   Sal I r-piggyBac act seq-Stu I (Tm = 60.5° C.;
Length = 27),
5'-AGGCCTATTCGATAAAGTTTTGTTAC-3'   (SEQ ID NO: 14)
   Stu I
```

Digest pCR2.1TOPO-PBAS.StuI by Sal I/Stu I and religate it into pDIE1TOPO3/LR-BGHA/L-GnT4A/R-GnT3 at Sal I/Stu I to produce pDIE1TOPO3/LR-BGHA/L-GnT4A/R-GnT3/LPBAS.

Digest using Xba I and religate the cassette in pXLBac II at Xba I REs site. Screen for BOTH insert and orientation. Remember pXLBacII will donate one PBAS, while the pDIE1TOPO3/LR-BGHA/L-GnT4A/R-GnT3/LPBAS insert will donate the other. The PBAS from pXLBacII MUST, therefore, be positioned downstream of the GnT3 gene as shown in FIG. 2.

FIG. 3 shows the strategy for construction of pBac vector encoding GnT2/GalT genes. Briefly, digest pDIE1-TOPO.3/LR-BGHA/L-PBAS/L-Gal3ST-R-Gn6ST with Spe I/Not I double digestion to remove the fragments (Gal3ST-IE1L-hr5-IE1R-Gn6ST). This will produce a plasmid pDIE1-TOPO.3/LR-BGHA/L-PBAS which will be used for inserting GnT2 and GalT cDNA.

Digest pDIE1-GnT2/GalT-DsRed1.TOPO4 by Spe I/Not I double digestion to produce two fragments.

Ligate one fragment from above one at a time in a two step manner in the plasmid pDIE1-TOPO.3/LR-BGHA/L-PBAS. See FIG. 3

The first step of ligation will produce pDIE1-TOPO.3/LR-BGHA/L-PBAS/Spe I-GnT2-Not I (1192 bp). This will be used in a second step of ligation wherein the $2^{nd}$ fragment will be inserted into pDIE1-TOPO.3/LR-BGHA/L-PBAS/Spe I-GnT2-Not I (1192 bp) at Not I to produce pDIE1-TOPO.3/LR-BGHA/L-PBAS/L-GnT2/R-GalT. Since the last step is not positional cloning check for the correct insert orientation. Use Sma I REs to confirm the right orientation of Not I fragment.

4. Once pDIE1-TOPO.3/LR-BGHA/L-PBAS/L-GnT2/R-GalT is ready, digest it with Xba I to remove the cassette LR-BGHA/L-PBAS/L-GnT2/R-GalT and religate it into Xba I position in pXLBACII as shown in FIG. 3.

Screen for BOTH insert and orientation. Remember pXL-BacII will donate one PBAS, while the LR-BGHA/L-GnT2/R-GalT/L-PBAS insert will donate the other. The PBAS from pXLBacII MUST, therefore, be positioned downstream of the GalT gene. See FIG. 3d.

The advantages offered by this new cell line for production of the influenza virus subunit vaccine, composed of recombinant HA's, are apparent. The most widely used flu vaccine in the United States and Europe is a mixture of three influenza viruses, which were produced in embryonated eggs, chemically inactivated, and then purified. One egg yields about enough virus for a single adult dose of flu vaccine. Hundreds of millions of doses are produced in seasonal fashion to meet seasonal demands in the Fall of each year. Thus, seasonal availability of embryonated eggs is a critical limitation in this manufacturing approach. Another limitation is that these vaccines can have residual egg proteins, which can cause allergic reactions in human patients. The use of recombinant subunit vaccine produced in the baculovirus-insect cell system as described herein circumvents both of these problems. The transgenic insect cell lines of the present invention produces a more authentic form of recombinant HA for use as a subunit vaccine. Its increased authenticity is likely to increase the acceptability, safety, and perhaps the efficacy of this vaccine.

Example II

Production of a New Insect Cell Line Designed to Produce Recombinant Glycoproteins with Humanized, Sulfated N-Glycans In the present example, an insect cell line designated SfSWT-7 was created by transformation of ExpresSf+® cells with mammalian Gn-TII, Gal-T, Gn6ST and Gal3ST genes in piggyBac vectors, as described in Example I and detailed in FIGS. 1A-1B and 3A-3D. The expression of these mammalian genes provides the enzymes needed to produce complex, biantennary, sulfated N-glycans on recombinant glycoproteins such as influenza hemagglutinin (HA), which can be produced by the expression of a separate foreign gene in insect cells. In preparation for the creation of this new insect cell line, two distinct dual piggyBac vectors were constructed using IE plasmid and dual piggyBac vector precursors (FIGS. 1A-1B and 3A-3D). One of these vectors encoded Gn-TII and Gal-T, while the other encoded Gn6ST and Gal3ST. These vectors were checked by restriction mapping and purified from scaled-up E. coli cultures.

Figure 4:
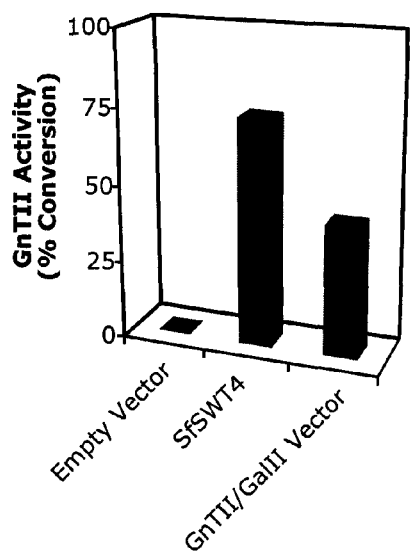
FIG. 4 provides graphs of transient expression assays showing pDIE1-TOPO.3/LR-BGHA/L-PBAS/LGnT2/RGalT is capable of inducing both N-acetylglucosaminyltransferase II (FIG. 4A) and β4-galactosyltranferase (FIG. 4B) activities.
Figure 4:
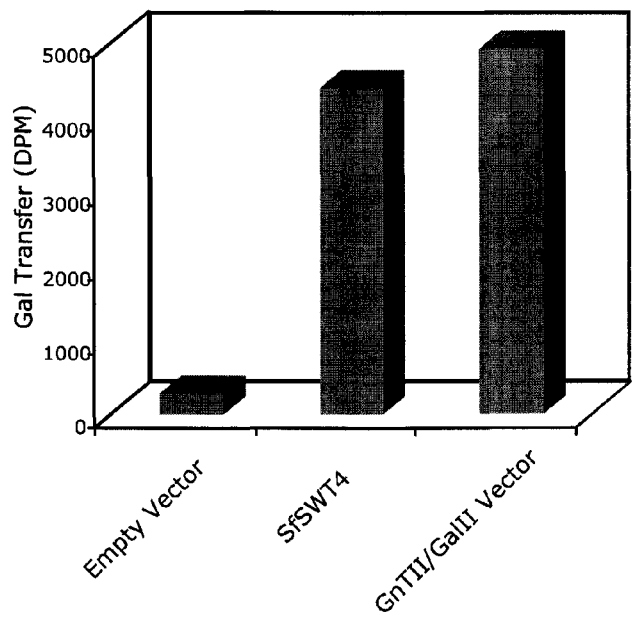

The vectors were subsequently expressed by transient transfection of insect cells and tested in functional assays for induction of the relevant activities, as previously described (12-15, 20, 22, 41, 45, 46). The results (FIG. 4) showed that insect cells transfected with the dual piggyBac vector (pDIE1-TOPO.3/LR-BGHA/L-PBAS/LGnT2/RGalT) encoding Gn-TII and Gal-T had these two new enzymatic activities, which are characteristic of human, but not insect protein N-glycosylation pathways. Each of the enzyme activities induced by this piggyBac vector, as shown by the results in FIG. 4, are prerequisite to the production of a recombinant form of rHA with humanized, sulfated N-glycans.

Figure 5:
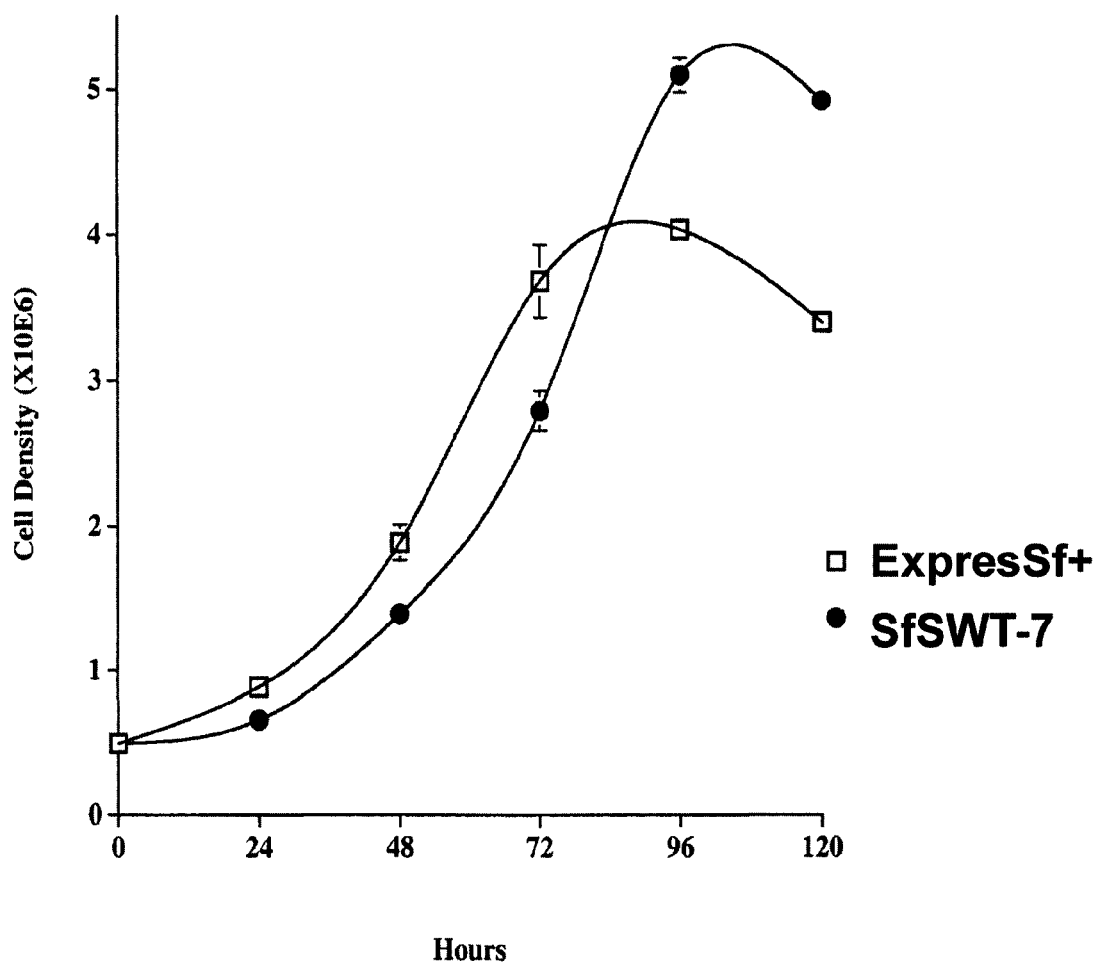
FIG. 5 is a graph of cellular growth curves showing SfSWT-7 cells (i.e., cells genetically transformed with pDIE1-TOPO.3/LR-BGHA/L-PBAS/LGnT2/RGalT and pDIE1-TOPO.3/LR-BGHA/LR-PBAS/LGal3ST/RGn6ST) have growth properties that are highly similar to the parental (i.e., ExpresSf+®) cell line.
Figure 6:
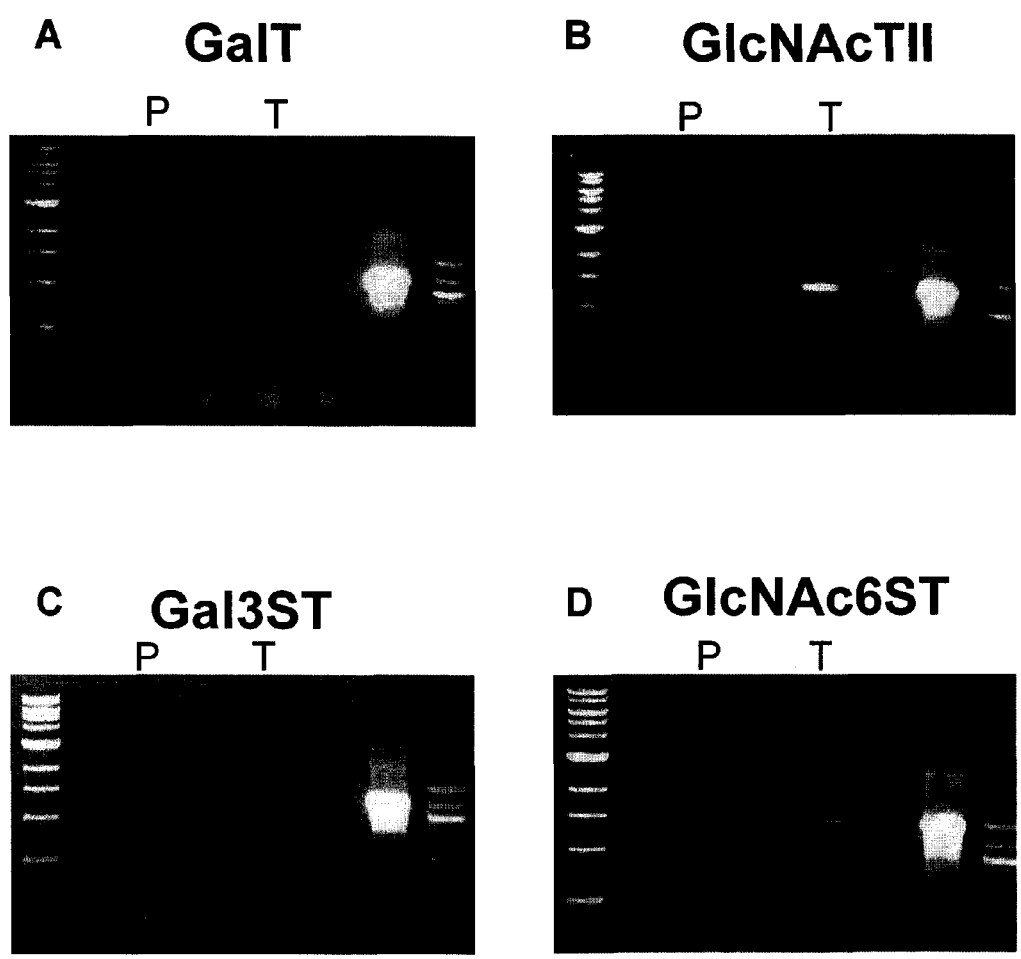
FIG. 6A-6D provides images of reverse-transcription PCR assay results showing SfSWT-7 cells express all four transgenes at the transcriptional level.

In subsequent experiments, the dual piggyBac vector encoding GalT and GnTII was co-introduced into cells with the dual piggyBac vector encoding the sulfotransferases Gal3ST and Gn6ST. As shown in FIG. 5, the growth properties of insect cells genetically transformed with these two vectors (1) pDIE1-TOPO.3/LR-BGHA/L-PBAS/LGnT2/RGalT and (2) pDIE1-TOPO.3/LR-BGHA/LR-PBAS/LGal3ST/RGn6ST (the resulting cells are referred to as "SfSWT-7") are comparable to the growth of the parental cell line, ExpresSf+®, over a 5 day period. Since there was no significant difference in replication, this indicates that the transformed cells have the ability to proliferate after the introduction of enzymes needed to produce humanized recombinant glycoproteins. Next, RT-PCR was used to test whether the transformed SfSWT-7 cells express the transgenes encoding the various glycosylation enzymes at the transcriptional level. The lanes marked "P" in FIG. 6, Panels A-D show that none of these genes were expressed by the parental cell line, ExpresSf+®, as expected. In contrast, the lanes marked "T" show that the transgenic cell line, SfSWT-7, expresses each of the glycosylation enzymes at the transcriptional level.

Figure 7:
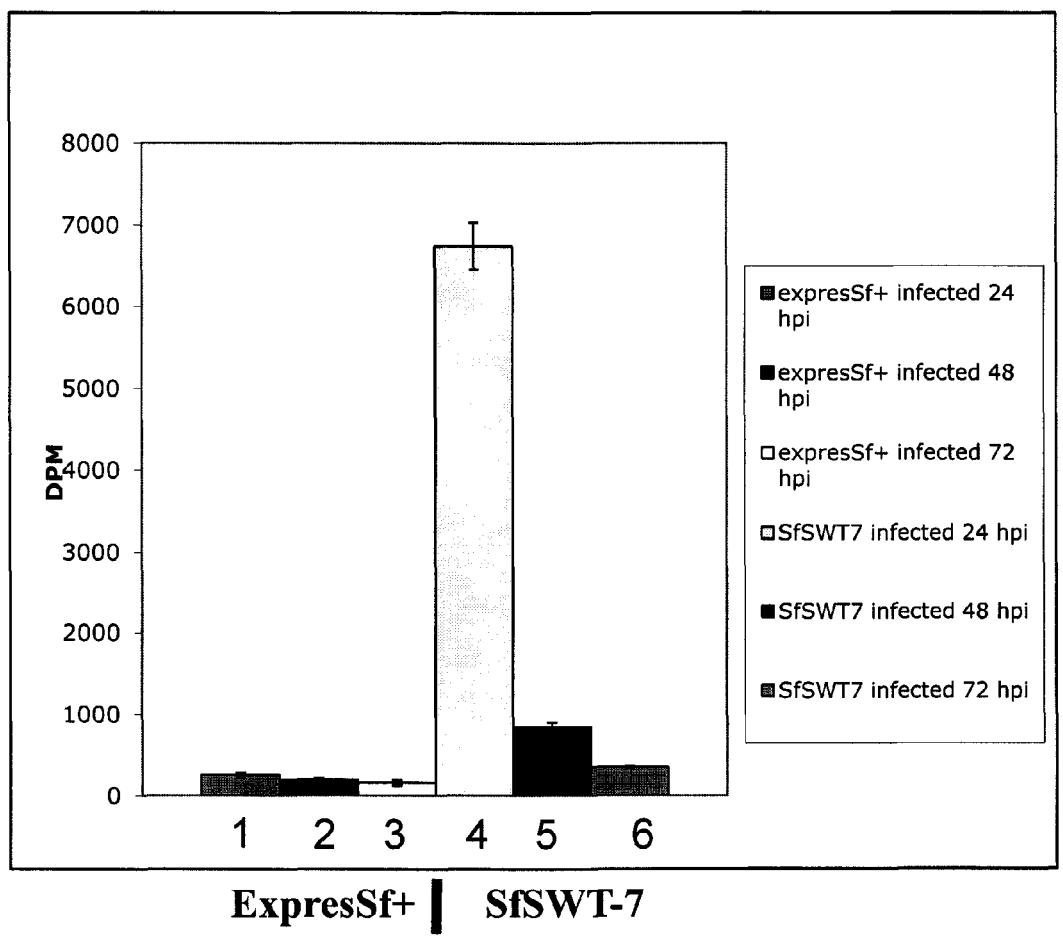
FIG. 7 is a graph of galactosyltransferase assay results showing SfSWT-7 cells contain galactosyltransferase activity.

Next, the parental ExpresSf+® and transgenic SfSWT-7 cells were assayed for galactosyltranferase activity using the same assay as was used in FIG. 4B. The results shown in FIG. 7 demonstrate that the SfSWT-7 cells, which harbor the four transgenes, have galactosyltransferase activity (see lane 4). Columns 1-3 of FIG. 7 show that the parental ExpresSf+® cells have no galactosyltransferase activity, as they scored only at the background levels of the assay. Columns 5 and 6 show that baculovirus infection of SfSWT-7 cells represses their galactosyltransferase activity, but they still have higher levels of activity than the parental cells even at 72 h post-infection.

Figure 8:
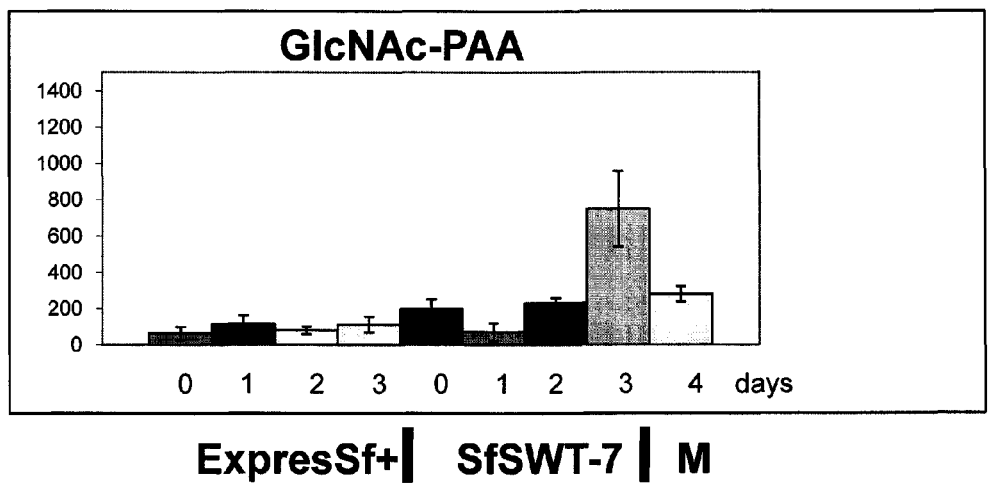
FIGS. 8A and 8B provide graphs of sulfotransferase assay results showing SfSWT-7 cells contain both Gal3 and Gn6-sulfotransferase activity.
Figure 8:
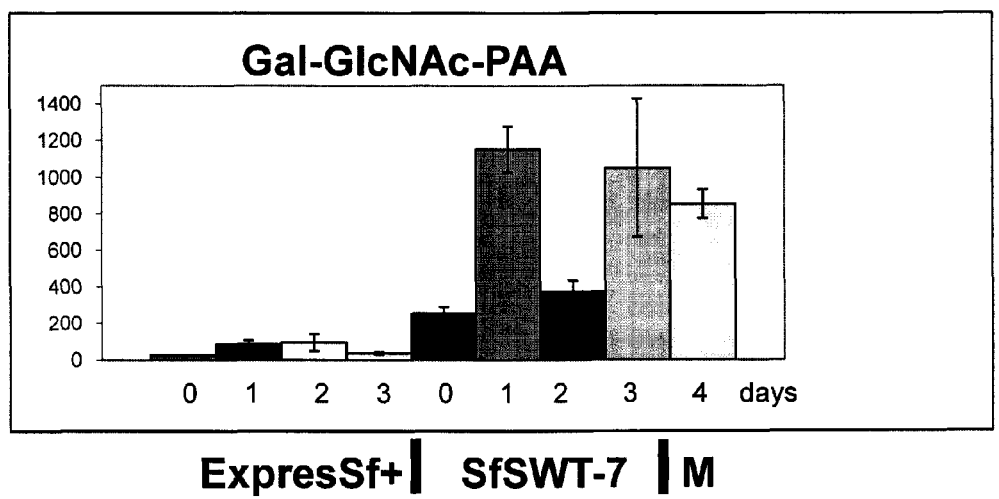

Sulfotransferase assays also were performed to assess these activities in the parental ExpresSf+® and transgenic SfSWT-7 cells. Panels A and B of FIG. 8 demonstrate that SfSWT-7 cells, which contain both sulfotransferase genes, have both Gal3 and Gn6 sulfotransferase activities. In contrast, the parental ExpresSf+® cells have neither activity, as both assays revealed only background levels. The different bars in FIG. 8 show the activity levels measured at 0, 1, 2, and 3 days post-infection, and the results demonstrate the impact of baculovirus infection on activity.

Production of a Model Foreign Glycoprotein by SfSWT-7 Cells

Figure 9:
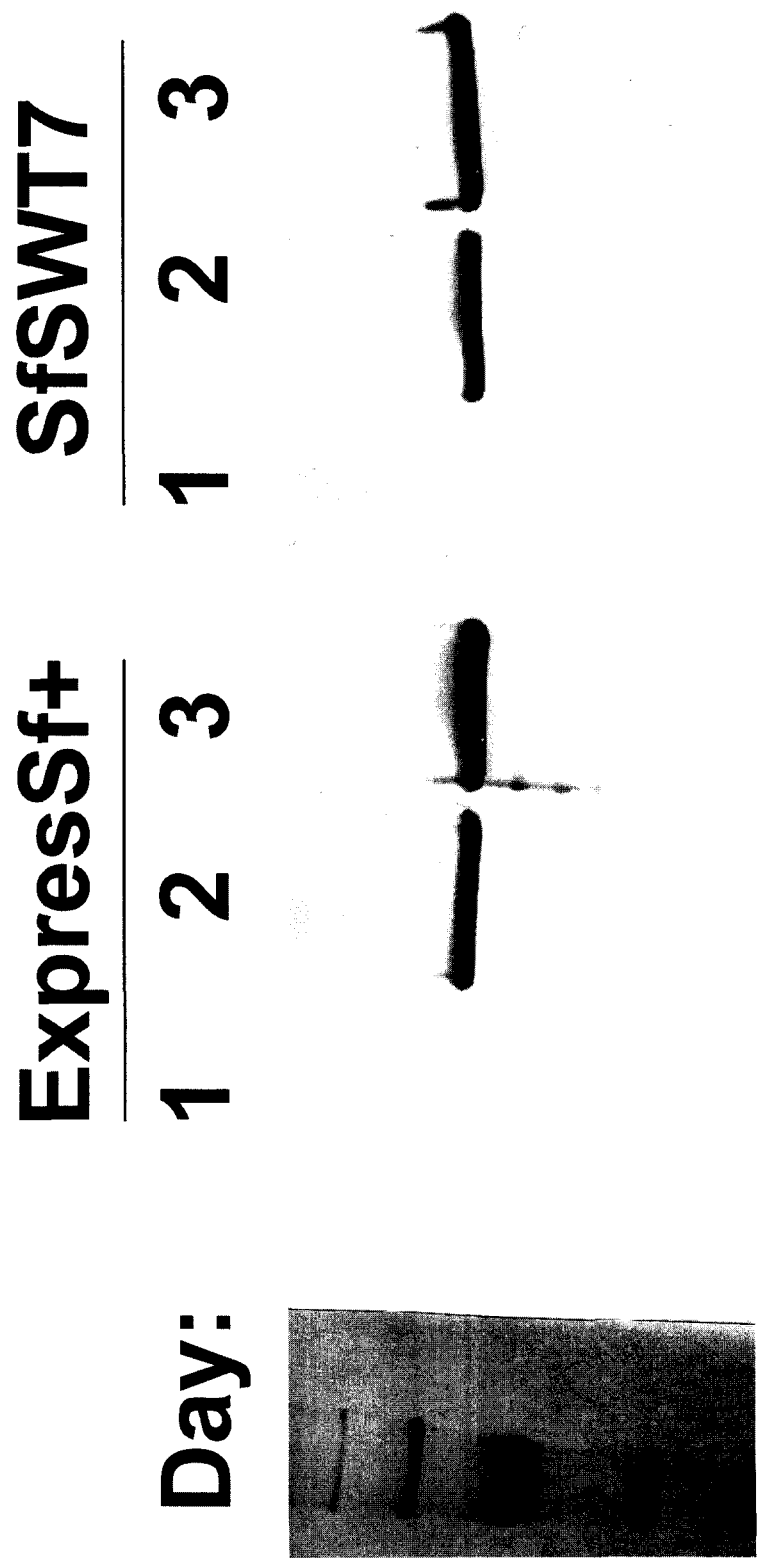
FIG. 9 provides images of recombinant glycoprotein production. The Western blotting assay results show SfSWT-7 cells can produce a model glycoprotein, GSTSfManI, at similar levels as the parental (ExpresSf+®) cell line.

The preceding assays established that the new transgenic insect cell line, SfSwt-7, which was transformed with four transgenes encoding mammalian genes involved in N-glycan processing (i.e., GalT, GnTII, Gal3ST and Gn6ST) have functional levels of each of these activities. Subsequently, the ability of these cells to produce recombinant glycoproteins was determined in comparison to the parental cell line. In FIG. 9, GST-SfManI, a glutathione-S-transferase-tagged Sf9 cell class I α-mannosidase protein, was used as the model to assess the levels of recombinant glycoprotein production provided by the transformed cells (Kawar et al., (2000). The results of Western blotting experiments with anti-GST as the primary antibody (FIG. 9) demonstrated that the transgenic SfSWT-7 and parental ExpresSf+ cells produced GST-SfManI at similar levels.

Production and Glycosylation of Influenza HA by SfSWT-7 Cells

Figure 10:
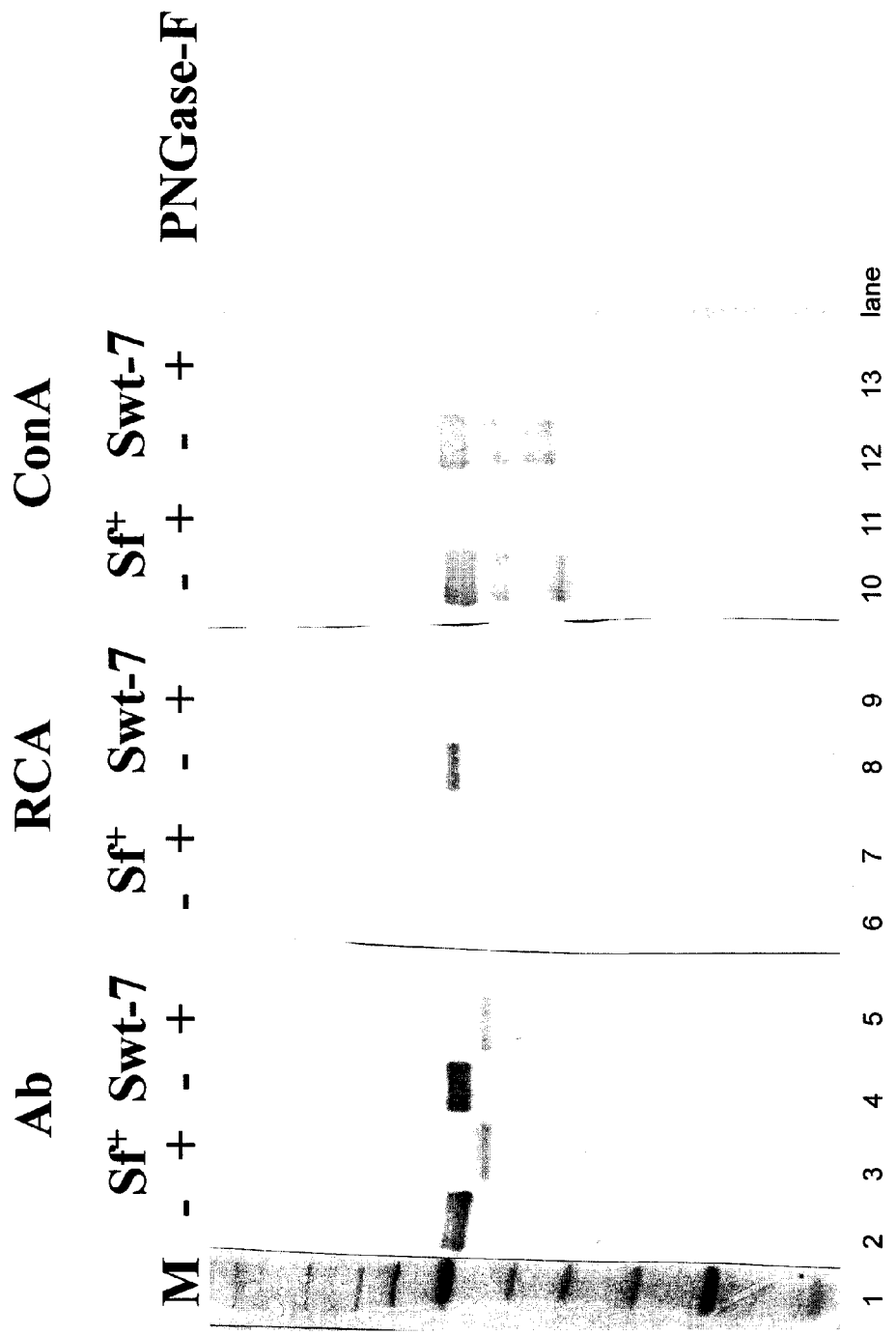
FIG. 10 provides images of recombinant influenza hemagglutinin production. Western & lectin blotting assay results showing SfSWT-7 cells can produce a differentially glycosylated form of rHA.

In subsequent work, the ability of the transgenic SfSWT-7 and parental ExpresSf+ cells to produce and glycosylate an influenza HA were compared. Recombinant HA was extracted, immunoprecipitated with a monoclonal antibody, and samples were quantified by Western blotting. Equivalent amounts of rHA were also assayed by lectin blotting assays, as described previously (Jarvis and Finn, (1996)). The results from the Western and lectin blotting assays shown in FIG. 10 demonstrate that the transformed SfSWT-7 cells can produce recombinant HA with humanized N-glycans (lane 8). Specifically, the band in Lane 8 of FIG. 10 shows that the Gal-binding lectin, *Ricinus communis* agglutinin ("RCA"), which binds β-linked galactose, interacts with the rHA produced by the cells transformed with Gn-TII, Gal-T, Gn6ST and Gal3ST, but not with the rHA produced by the parental ExpresSf+® cells (FIG. 10, lane 6). FIG. 10 shows that the rHA produced by the SfSWT7 cells contain glycans that terminate with lactosamine, which is a characteristic of glycans on the natural human form of HA. In combination with the results of the sulfotransferase activity assays shown in FIG. 8, these results demonstrate that the baculovirus-insect cell expression system can be engineered to produce sulfated complex N-glycans.

LITERATURE CITED

1. Ailor, E., et al. 2000. N-glycan patterns of human transferrin produced in *Trichoplusia ni* insect cells: effects of mammalian galactosyltransferase. Glycobiology 10:837-847.
2. Altmann, F., E. Staudacher, I. B. Wilson, and L. Marz. 1999. Insect cells as hosts for the expression of recombinant glycoproteins. Glycoconj. J. 16:109-123.
3. Arbatsky, N. P., et al. 1988. The carbohydrate chains of influenza virus hemagglutinin. Carbohydr. Res. 178:165-181.
4. Aumiller, J. J., J. R. Hollister, and D. L. Jarvis. 2003. A transgenic lepidopteran insect cell line engineered to produce CMP-sialic acid and sialoglycoproteins. Glycobiology 13:497-507.
5. Butters, T. D., R. C. Hughes, and P. Vischer. 1981. Steps in the biosynthesis of mosquito cell membrane glycoproteins and the effects of tunicamycin. Biochim. Biophys. Acta 640:672-686.
6. Cambi, A., M. Koopman, and C. G. Figdor. 2005. How C-type lectins detect pathogens. Cell. Microbiol. 7:481-488.
7. Deom, C. M., and I. T. Schulze. 1985. Oligosaccharide composition of an influenza virus hemagglutinin with host-determined binding properties. J. Biol. Chem. 260:14771-14774.
8. Handler, A. M. 2002. Use of the piggyBac transposon for germ-line transformation of insects. Insect Biochem. Mol. Biol. 32:1211-1220.
9. Hardy, M. R., and R. R. Townsend. 1994. High-pH anion-exchange chromatography of glycoprotein-derived carbohydrates. Meth. Enzymol. 230:208-225.
10. Harrison, R. L., and D. L. Jarvis. 2006. Transforming lepidopteran insect cells for continuous recombinant protein expression, in press. In D. W. Murhammer (ed.), Baculovirus Expression Protocols. Humana Press, Clifton, N.J.
11. Harrison, R. L., and D. L. Jarvis. 2006. Transforming lepidopteran insect cells for improved protein processing, in press. In D. W. Murhammer (ed.), Baculovirus Expression Protocols. Humana Press, Clifton, N.J.
12. Hill, D. R., J. J. Aumiller, X. Shi, and D. L. Jarvis. 2006. Isolation and analysis of a baculovirus vector that supports recombinant glycoprotein sialylation by SfSWT-1 cells cultured in serum-free medium. Biotechnol. Bioengr. 95:37-47.
13. Hollister, J., and D. L. Jarvis. 2001. Engineering lepidopteran insect cells for sialoglycoprotein production by genetic transformation with mammalian β1,4-galactosyltransferase and α2,6-sialyltransferase genes. Glycobiology 11: 1-9.
14. Hollister, J. R., E. Grabenhorst, M. Nimtz, H. O. Conradt, and D. L. Jarvis. 2002. Engineering the protein N-glycosylation pathway in insect cells for production of biantennary, complex N-glycans. Biochemistry 41:15093-15104.
15. Hollister, J. R., J. H. Shaper, and D. L. Jarvis. 1998. Stable expression of mammalian beta 1,4-galactosyltransferase extends the N-glycosylation pathway in insect cells. Glycobiology 8:473-480.
16. Hsieh, P., and P. W. Robbins. 1984. Regulation of asparagine-linked oligosaccharide processing. Oligosaccharide processing in *Aedes albopictus* mosquito cells. J. Biol. Chem. 259:2375-2382.
17. Jacob, G. S., and P. Scudder. 1994. Glycosidases in structural analysis, p. 280-299. In W. Lennarz and G. Hart (ed.), Guide to Techniques in Glycobiology, vol. 230. Academic Press, Inc., San Diego.
18. Jarvis, D. L. 1997. Baculovirus expression vectors, p. 389-431. In L. K. Miller (ed.), The Baculoviruses. Plenum Press, New York.
19. Jarvis, D. L., and E. E. Finn. 1995. Biochemical analysis of the N-glycosylation pathway in baculovirus-infected lepidopteran insect cells. Virology 212:500-511.
20. Jarvis, D. L., and E. E. Finn. 1996. Modifying the insect cell N-glycosylation pathway with immediate early baculovirus expression vectors. Nat. Biotechnol. 14:1288-1292.
21. Jarvis, D. L., J. A. Fleming, G. R. Kovacs, M. D. Summers, and L. A. Guarino. 1990. Use of early baculovirus promoters for continuous expression and efficient processing of foreign gene products in stably transformed lepidopteran cells. Bio/Technology 8:950-955.
22. Jarvis, D. L., D. Howe, and J. J. Aumiller. 2001. Novel baculovirus expression vectors that provide sialylation of recombinant glycoproteins in lepidopteran insect cells. J. Virol. 75:6223-6227.
23. Jarvis, D. L., and M. D. Summers. 1989. Glycosylation and secretion of human tissue plasminogen activator in recombinant baculovirus-infected insect cells. Mol. Cell. Biol. 9:214-223.
24. Jarvis, D. L., C. Weinkauf, and L. A. Guarino. 1996. Immediate early baculovirus vectors for foreign gene expression in transformed or infected insect cells. Prot. Expr. Purif. 8:191-203.
25. Karaivanova, V. K., and R. G. Spiro. 1998. Sulphation of N-linked oligosaccharides of vesicular stomatitis and influenza virus envelope glycoproteins: host cell specificity, subcellular localization and identification of substituted saccharides. Biochem. J. 329:511-518.
26. Kato, Y., and R. G. Spiro. 1989. Characterization of a thyroid sulfotransferase responsible for the 3-O-sulfation of terminal beta-D-galactosyl residues in N-linked carbohydrate units. J. Biol. Chem. 264:3364-3371.
27. Keil, W., et al. 1985. Carbohydrates of influenza virus. Structural elucidation of the individual glycans of the FPV hemagglutinin by two-dimensional 1H n.m.r. and methylation analysis. EMBO J. 4:2711-2720.
28. Keler, T., V. Ramakrishna, and M. W. Fanger. 2004. Mannose receptor-targeted vaccines. Exp. Op. Biol. Ther. 4:1953-1962.
29. Kitts, P. A., and R. D. Possee. 1993. A method for producing recombinant baculovirus expression vectors at high frequency. Biotechniques 14:810-817.
30. Kornfeld, R., and S. Kornfeld. 1985. Assembly of asparagine-linked oligosaccharides. Ann. Rev. Biochem. 54:631-664.
31. Kuroda, K., H. Geyer, R. Geyer, W. Doerfler, and H. D. Klenk. 1990. The oligosaccharides of influenza virus hemagglutinin expressed in insect cells by a baculovirus vector. Virology 174:418-429.
32. Lee, J., S. H. Park, and P. Stanley. 2002. Antibodies that recognize bisected complex N-glycans on cell surface glycoproteins can be made in mice lacking N-acetylglucosaminyltransferase III. Glycoconj. J. 19:211-219.
33. Luckow, V. A., S. C. Lee, G. F. Barry, and P. O. Olins. 1993. Efficient generation of infectious recombinant baculoviruses by site-specific transposon-mediated insertion of foreign genes into a baculovirus genome propagated in *Escherichia coli*. J. Virol. 67:4566-4579.
34. McGreal, E. P., L. Martinez-Pomares, and S. Gordon. 2004. Divergent roles for C-type lectins expressed by cells of the innate immune system. Mol. Immunol. 41:1109-1121.
35. Mir-Shekari, S. Y., D. A. Ashford, D. J. Harvey, R. A. Dwek, and I. T. Schulze. 1997. The glycosylation of the influenza A virus hemagglutinin by mammalian cells. A site-specific study. J. Biol. Chem. 272:4027-4036.
36. Montreuil, J., J. F. G. Vliegenthart, and H. Schachter. 1995. Glycoproteins, vol. 29a. Elsevier, Amsterdam.
37. Niemann, H., et al. 1985. The major oligosaccharides in the large subunit of the hemagglutinin from fowl plague virus, strain Dutch. Structure elucidation by one-dimensional and two-dimensional 1H nuclear magnetic resonance and by methylation analysis. Eur. J. Biochem. 146:523-532.
38. O'Reilly, D. R., L. K. Miller, and V. A. Luckow. 1992. Baculovirus expression vectors. W.H. Freeman and Company, New York.
39. Packer, N. H., M. A. Lawson, D. R. Jardine, and J. W. Redmond. 1998. A general approach to desalting oligosaccharides released from glycoproteins. Glycoconj. J. 15:737-747.
40. Pfeifer, T. A. 1998. Expression of heterologous proteins in stable insect cell culture. Curr. Op. Biotechnol. 9:518-521.
41. Seo, N. S., J. R. Hollister, and D. L. Jarvis. 2001. Mammalian glycosyltransferase expression allows sialoglycoprotein production by baculovirus-infected insect cells. Prot. Expr. Purif. 22:234-241.
42. Shi, X., R. L. Harrison, J. R. Hollister, M. J. Fraser, and D. L. Jarvis. 2006. Construction and characterization of new piggyBac vectors for constitutive or inducible expression of heterologous gene pairs and the identification of a previously unrecognized activator sequence in piggyBac. BMC Biotechnology Submitted.
43. Spiro, R. G., Y. Yasumoto, and V. Bhoyroo. 1996. Characterization of a rat liver Golgi sulphotransferase responsible for the 6-O-sulphation of N-acetylglucosamine residues in beta-linkage to mannose: role in assembly of sialylgalactosyl-N-acetylglucosamine 6-sulphate sequence of N-linked oligosaccharides. Biochem. J. 319:209-216.
44. Summers, M. D., and G. E. Smith. 1987. A manual of methods for baculovirus vectors and insect cell culture procedures. Tx. Ag. Expt. Stn. Bull. No. 1555.
45. Taniguchi, N., A. Nishikawa, S. Fujii, and J. G. Gu. 1989. Glycosyltransferase assays using pyridylaminated acceptors: N-acetylglucosaminyltransferase III, IV, and V. Meth. Enzymol. 179:397-408.
46. Tomiya, N., et al. 2003. Complex-type biantennary N-glycans of recombinant human transferrin from *Trichoplusia ni* insect cells expressing mammalian β1,4-galactosyltransferase and β1,2-N-acetylglucosaminyltransferase II. Glycobiology 13:23-34.
47. Treanor, J. J., et al. 2006. Dose-related safety and immunogenicity of a trivalent baculovirus-expressed influenza-virus hemagglutinin vaccine in elderly adults. J. Infect. Dis. 193:1223-1228.

48. Varki, A., et al. 1999. Essentials of Glycobiology. Cold Spring Harbor Press, Cold Spring Harbor, N.Y.
49. Vaughn, J. L., R. H. Goodwin, G. J. Thompkins, and P. McCawley. 1977. The establishment of two insect cell lines from the insect *Spodoptera frugiperda* (Lepidoptera: Noctuidae). In Vitro 13:213-217.
50. Ward, C. W., P. A. Gleeson, and T. A. Dopheide. 1980. Carbohydrate composition of the oligosaccharide units of the haemagglutinin from the Hong Kong influenza virus A/Memphis/102/72. Biochem. J. 189:649-652.
51. Warren, L. 1963. The distribution of sialic acids in nature. Comp. Biochem. Physiol. 10:153-171.
52. Wolff, M. W., D. W. Murhammer, D. L. Jarvis, and R. J. Linhardt. 1999. Electrophoretic analysis of glycoprotein glycans produced by lepidopteran insect cells infected with an immediate early recombinant baculovirus encoding mammalian β1,4-galactosyltransferase. Glycoconj. J. 16:753-756.
53. Wormald, M. R., et al. 1997. Variations in oligosaccharide-protein interactions in immunoglobulin G determine the site-specific glycosylation profiles and modulate the dynamic motion of the Fc oligosaccharides. Biochemistry 36:1370-1380.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A transgenic insect cell for the production of at least one protein of interest comprising sulfated complex N-glycans, said insect cell comprising at least one nucleic acid molecule encoding at least two modifying enzymes selected from the group consisting of:
   i) —N-acetylglucosaminyltransferase II;
   ii) —N-acetylglucosaminyltransferase III;
   iii) —N-acetylglucosaminyltransferase IV;
   iv) -Beta 1,4-Galactosyltransferase;
   v) —N-acetylglucosamine-6-O-sulfotransferase;
   vi) -Galactose-3-O-sulfotransferase; and
   vii) —N-acetylglucosaminyltransferase V, said cell comprising at least nucleic acids encoding i) and v) or i) and vi) and optionally comprising at least one additional nucleic acid molecule encoding said at least one protein of interest, wherein said modifying enzymes catalyze the formation of sulfated complex N-glycans on said protein of interest.

2. The cell of claim 1 wherein said protein of interest is heterologous.

3. The cell of claim 1, wherein said at least one protein of interest is selected from the group consisting of a subunit vaccine, antibody, cytokine, blood clotting factor, anticoagulant, viral antigen, enzyme, receptor, vaccine, and hormone.

4. The cell of claim 1, wherein said nucleic acids are operably linked to at least one expression control sequence.

5. The cell of claim 4, wherein said expression control sequence comprises a promoter for constitutive expression.

6. The cell of claim 4, wherein said expression control sequence comprises an inducible promoter.

7. The cell of claim 1, wherein the cell is selected from the group consisting of a lepidopteran, coleopteran, and hymenopteran cell.

8. The cell claim 7, selected from the group consisting of Sf9, Sf21, ExpreSf+®, Tn368, BTI-Tn5B-1, HighFive®, BmN, Schneider 2, S2, D2 and KC cells.

9. The cell of claim 5, wherein the constitutive promoter is derived from a baculovirus early gene, ie0, ie1, ie2, PE-38 or 39K.

10. The transgenic insect cell of claim 6, wherein the inducible promoter comprises a baculovirus-specific late, very late promoter, an hsp70 promoter, a metallothionein promoter and a tetracycline-regulated promoter.

11. The cell of claim 1, wherein the nucleic acid encoding said at least one protein of interest is not expressed until the transgenic insect cell is infected with a baculovirus.

12. The cell of claim 1, wherein said nucleic acids are in a vector selected from the group consisting of a plasmid vector, a viral vector, a piggyBac vector, a retroviral vector, a baculoviral vector, and a lentiviral vector.

13. The cell of claim 1, wherein said nucleic acids are in a piggyBac vector.

14. The cell of claim 1, wherein said cell is a lepidopteran cell comprises a combination of modifying enzymes wherein the combination is selected from the group consisting of:
   a) enzymes i), iv) and v),
   b) enzymes i), iv) and vi),
   c) enzymes i), iv), v), and vi),
   d) enzymes i), ii), iv), and v),
   e) enzymes i), ii), iv) and vi),
   f) enzymes i), ii), iv), v) and vi),
   g) enzymes i), iii), iv), and v),
   h) enzymes i), iii), iv), vi),
   i) enzymes i), iii), iv), v), vi),
   j) enzymes i), iii), v), and vii),
   k) enzymes i), iii), iv), vi), and vii), and
   l) enzymes i), iii), iv), v), vi), and vii).

15. The cell of claim 1 wherein said cell comprises nucleic acid encoding the modifying enzymes:
   a) N-acetylglucosaminyltransferase II;
   b) Beta 1,4-Galactosyltransferase;
   c) N-acetylglucosamine-6-O-sulfotransferase; and
   d) Galactose-3-O-sulfotransferase.

16. The cell of claim 1, wherein said protein of interest is influenza Hemagglutinin.

17. The cell of claim 1, wherein said at least one nucleic acid molecule is present in more than one copy in said cell.

18. A method for producing at least one protein of interest comprising sulfated complex N-glycans, comprising:
   a) providing the cell of claim 1;
   b) introducing a nucleic acid encoding said at least one protein of interest into the cell of a); and
   c) incubating under conditions which result in production of said enzymes and said protein of interest, said at least one protein of interest comprising sulfated complex N-glycans.

19. The method of claim 18, further comprising isolation of said protein of interest.

20. The method of claim 18, wherein said protein of interest is selected from the group consisting of an antibody, cytokine, blood clotting factor, anticoagulant, viral antigen, enzyme, receptor, vaccine, and hormone.

21. The method of claim 18, wherein said protein of interest is selected from the group consisting of influenza hemagglutinin, HIV gp 120 and VSV g protein.

22. The method of claim 18, wherein said at least one protein of interest comprises a subunit vaccine.

23. The method of claim 22, wherein said vaccine is an influenza hemagglutinin.

24. A kit for the production of at least one protein of interest comprising sulfated complex N-glycans comprising; at least one nucleic acid molecule encoding at least two modifying enzymes selected from the group consisting of:
   i) —N-acetylglucosaminyltransferase II;
   ii) —N-acetylglucosaminyltransferase III;
   iii) —N-acetylglucosaminyltransferase IV;
   iv) -Beta 1,4-Galactosyltransferase;
   v) —N-acetylglucosamine-6-O-sulfotransferase;
   vi) -Galactose-3-O-sulfotransferase; and
   vii) —N-acetylglucosaminyltransferase V, said kit comprising at least nucleic acids encoding i) and v) or i) and vi).

25. The kit of claim 24, further comprising lepidopteran insect cells.

26. The kit of claim 24, further comprising a nucleic acid encoding at least one protein of interest.

27. The kit of claim 26, wherein said nucleic acid encoding said protein of interest is in a separate expression vector.

28. The kit of claim 26, wherein said protein of interest is selected from the group consisting of an antibody, cytokine, blood clotting factor, anticoagulant, viral antigen, enzyme, receptor, vaccine, and hormone.

29. The kit of claim 26, wherein said protein of interest is selected from the group consisting of influenza hemagglutinin, HIV gp120 and VSV G protein.

30. The kit of claim 26, wherein said protein of interest is a subunit vaccine.

31. The kit of claim 26, wherein said vaccine is an influenza hemagglutinin.

32. The transgenic insect cell of claim 1 which is a lepidopteran cell.

\* \* \* \* \*